United States Patent

DiMaio et al.

[11] Patent Number: 6,034,097
[45] Date of Patent: Mar. 7, 2000

[54] ISOQUINOLINES USEFUL AS ANALGESICS

[75] Inventors: John DiMaio, Montreal; Wuyi Wang, St-Laurent, both of Canada

[73] Assignee: Astra AB, Sweden

[21] Appl. No.: 08/930,867

[22] PCT Filed: Feb. 25, 1997

[86] PCT No.: PCT/SE97/00315

§ 371 Date: Oct. 6, 1997

§ 102(e) Date: Oct. 6, 1997

[87] PCT Pub. No.: WO97/31940

PCT Pub. Date: Sep. 4, 1997

[30] Foreign Application Priority Data

Feb. 28, 1996 [SE] Sweden .................................. 9600769

[51] Int. Cl.[7] .......................... A61K 31/47; A61K 38/05; C07D 217/26; C07D 217/14

[52] U.S. Cl. ........................ 514/308; 546/145; 546/176

[58] Field of Search .................. 514/308; 546/176, 546/145

[56] References Cited

U.S. PATENT DOCUMENTS

| | | | |
|---|---|---|---|
| 4,599,325 | 7/1986 | Hansen, Jr. et al. | 514/19 |
| 5,602,099 | 2/1997 | Schiller | 514/18 |
| 5,648,333 | 7/1997 | Henke et al. | 514/2 |

FOREIGN PATENT DOCUMENTS

| | | |
|---|---|---|
| 2090171 | 8/1994 | Canada . |
| 618221 | 10/1994 | European Pat. Off. . |
| WO 94/15959 | 7/1994 | WIPO . |
| 9606855 | 3/1996 | WIPO . |
| WO 96/06855 | 3/1996 | WIPO . |

OTHER PUBLICATIONS

Lord, et al., "Endogenous Opioid Peptides: Multiple Agonists and Receptors," *Nature* 267:495–499 (1977).
Martin, et al., "The Effects of Morphine– and Nalorphine–Like Drugs in the Nondependent and Morphine–Dependent Chronic Spinal Dog," *J. Pharmacol. Exper. Ther.* 197:517–532 (1976).
Schiller, et al., "Four Different Types of Opioid Peptides with Mixed μ Antagonist/δ Agonist Properties," *Analgesia* 1:703–706 (1995).
Carpenter et al. J. Am. Chem. Soc. (1994), 116(19), 8450–8.

Primary Examiner—Mark L. Berch
Attorney, Agent, or Firm—Michael A. Sanzo; Vinson & Elkins L.L.P.

[57] ABSTRACT

The present invention is directed to compounds that act as analgesics and that have the structure of formula (I):

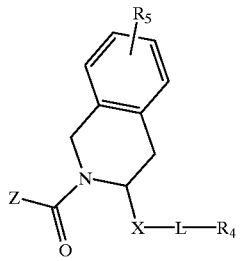

(I)

wherein;
Z is

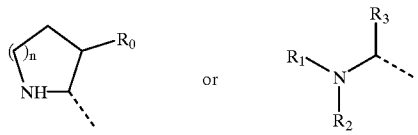

wherein,
n is 1 or 2, and $R_0$ is $C_{6-12}$ aryl or $C_{7-8}$ aralkyl; or
$R_1$ is selected from the group consisting of hydrogen; —NH—$C_{1-6}$ alkyl; $C_{1-6}$ alkyl; $C_{6-12}$ aryl; $C_{7-18}$ aralkyl; arginyl; and $R_{30}$NHC(=NH)—, wherein $R_{30}$ is hydrogen, $C_{6-12}$ aryl, $C_{7-18}$ aralkyl, or $C_{1-6}$ alkyl;
$R_2$ is hydrogen; $C_{1-6}$ alkyl; or OH;
$R_3$ is $C_{6-12}$ aryl; $C_{7-18}$ aralkyl; —$CH_2$—$C_6H_2R_8R_9$; or —$CH_2$—$OHC_6HR_8R_9$, wherein each of $R_8$ and $R_9$ is independently, or hydrogen;
$R_4$ $C_{6-12}$ aryl; $C_{7-18}$ aralkyl; $C_{1-12}$ alkyl; or a substituted or unsubstituted cyclohexyl;
$R_5$ is $C_{1-6}$ alkyl; hydrogen; OH; halogen; SH; $NO_2$; $NH_2$; —NH—$C_{1-6}$ alkyl; $NH_2C$ (=NH—; $NH_2C$ (=NH)—NH—; $COOR_{31}$, wherein, $R_{31}$ is hydrogen, or $C_{1-6}$ alkyl;
X is $CH_2NHC(O)$—; $CH_2NHC(O)O$; —C(O)NH—; or $CH_2NH$—; and
L is a $C_{1-12}$ alkylene chain which can be substituted with at least one substituent selected from the group consisting of; a $C_3$–$C_{12}$ cycloalkyl containing at least one heteroatom; $C_{1-6}$ alkyl; $OR_{31}$; —$NHC(O)R_{33}$; —$OC(O)R_{34}$ —$NHR_{35}$ wherein; and $NR_6R_7$;
with the proviso that when $R_5$ is hydrogen, Z is

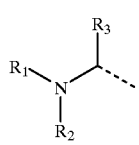

and X is —C(O)NH—, or —$CH_2NH$—, then L is a $C_{1-12}$ alkyl chain substituted with at least one substituent selected from the group consisting of; a $C_3$–$C_{12}$ cycloalkyl containing at least one heteroatom; $C_{1-6}$ alkyl; $OR_{31}$; $SR_{32}$; —NHC$(O)R_{33}$; —$OC(O)R_{34}$, —$NHR_{35}$; and $NR_6R_7$.

20 Claims, No Drawings

ISOQUINOLINES USEFUL AS ANALGESICS

This application is a 371 of PCT/SE97/00315.

FIELD OF THE INVENTION

The present invention is concerned with compounds that can act as analgesic.

BACKGROUND OF THE INVENTION

Many endogenous peptides of mammalian and amphibian origin bind to specific opioid receptors and elicit an analgesic response similar to classic narcotic opiates. Many different types of opioid receptors have been shown to coexist in higher animals. For example, see W. Martin et al., *J. Pharmacol. Exp. Ther.*, 197, p. 517(1975); and J. Lord et al., *Nature(London)*, 257, p. 495(1977). Three different types of opioid receptors have been identified. The first, $\mu$, shows a differentiating affinity for enkephalin-like peptides. The second, $\delta$, shows enhanced selectivity for morphine and other poly-cyclic alkaloids. The third, $\kappa$, exhibits equal affinity for either group of the above ligands and preferential affinity for dynorphin. In general, the $\mu$-receptors seem to be more involved with analgesic effects. The $\delta$-receptors appear to deal with behavioral effects, although the $\delta$ and the $\kappa$-receptors may also mediate analgesia.

Each opioid receptor, when coupled with an opiate, causes a specific biological response unique to that type of receptor. When an opiate activates more than one receptor, the biological response for each receptor is affected, thereby producing side effects. The less specific and selective an opiate may be, the greater the chance of causing increased side effects by the administration of the opiate.

In the prior art, opiates, opioid peptides, and analogs thereof, have either failed to demonstrate, or have demonstrated a limited degree of specificity and selectivity for the type of receptor, or receptors, to which they bind.

The primary site of action of analgesic opioids is the central nervous system (CNS). Conventional narcotic analgesics are normally quite hydrophobic and thus are extremely well-suited to permeate lipid membranes, such as the blood-brain barrier. Due to this physical capability, analgesics tend to bind with opioid receptors within the central nervous system in the brain. However, they do not necessarily bind with a homogeneous receptor subtype. This binding causes medically undesirable side effects to occur.

Opiates can cause serious and potentially fatal side effects. Side effects such as respiratory depression, tolerance, physical dependence capacity, and precipitated withdrawal syndrome are caused by nonspecific interactions with central nervous system receptors. See K. Budd, In *International Encyclopedia of Pharmacology and Therapeutics*; N. E. Williams and H. Wilkinson, Eds., Pergammon: (Oxford), 112, p.51 (1983). Therefore, opioid analgesics acting principally through opioid receptors in the peripheral nervous system would not be expected to cause similar unwanted side effects as those side effects associated with opioid analgesics affecting the central nervous system.

To date, one of the few classes of agents known to exert peripheral analgesic effects are non-steroidal anti-inflammatory agents, such as aspirin, ibuprofen, and ketorolac. These agents do not interact with opioid receptors but are known to inhibit cyclooxygenase and attenuate prostaglandin synthesis. These weak analgesics do not have centrally mediated side effects, but they can cause other side effects such as ulcerations of the gastro-intestinal tract.

There is therefore a need for opioid analgesic that can substantially affect the peripheral nervous system and therefore overcome some of the disadvantages of conventional opiates by substantially preventing unwanted side effects from occurring.

There is therefore a need to provide opioid-like peptides which act peripherally but substantially avoid the unwanted side effects associated with conventional peripherally acting analgesics.

There is also a need for opioid analgesic that can be administered orally.

SUMMARY OF THE INVENTION

The present invention provides analgesic compounds of general formula (I):

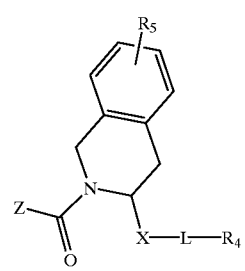

(I)

wherein;

Z is

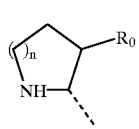 or 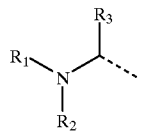

wherein;

n is 1 or 2, and $R_0$ is $C_{6-12}$ aryl or $C_{7-18}$ aralkyl;

$R_1$ is selected from the group consisting of hydrogen; —NH—$C_{1-6}$ alkyl; $C_{1-6}$ alkyl; $C_{6-12}$ aryl; $C_{7-18}$ aralkyl; arginyl; and $R_{30}$NHC(=NH)—, wherein, $R_{30}$ is hydrogen, $C_{6-12}$ aryl, $C_{7-18}$ aralkyl, or $C_{1-6}$ alkyl;

$R_2$ is hydrogen; $C_{1-6}$ alkyl; or OH;

$R_3$ is $C_{6-12}$ aryl; or $C_{6-18}$ aralkyl;

$R_4$ is $C_{6-12}$ aryl; $C_{7-18}$ aralkyl; or $C_{1-12}$ alkyl;

$R_5$ is $C_{1-6}$ alkyl; hydrogen; OH; halogen; SH; $NO_2$; $NH_2$; —NH—$C_{1-6}$ alkyl; $NH_2C(=NH)$—; $NH_2C(=NH)$—NH—; —COOR$_{31}$, wherein, $R_{31}$ is hydrogen, or $C_{1-6}$ alkyl;

X is —$CH_2$NHC(O)—; —$CH_2$NHC(O)O—; —C(O) NH—; or —$CH_2$NH—;

L is a $C_{1-12}$ alkyl chain which can be substituted with at least one substitutent selected from the group consisting of cyclic moeity; $C_{1-6}$ alkyl; $OR_{31}$ wherein, $R_{31}$ is hydrogen or $C_{1-6}$ alkyl; $SR_{32}$, wherein, $R_{32}$ is hydrogen or $C_{1-6}$ alkyl; —NHC(O)$R_{33}$ wherein, $R_{33}$ is $C_{6-12}$ aryl, $C_{7-18}$ aralkyl or $C_{1-6}$ alkyl; —OC(O)$R_{34}$ wherein, $R_{34}$ is hydrogen, $C_{6-12}$ aryl, $C_{7-18}$ aralkyl, $C_{1-6}$ alkyl, —NHR$_{35}$ wherein, $R_{35}$ is hydrogen, $C_{6-12}$ aryl or $C_{1-6}$ alkyl; and $NR_6R_7$, wherein each of $R_6$ and $R_7$ is independently hydrogen or $C_{1-6}$ alkyl;

with the proviso that when $R_5$ is hydrogen, Z is

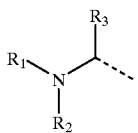

and X is —C(O)NH—, or —CH$_2$NH—; that L is a $C_{1-12}$ alkyl chain substituted with at least one substitutent selected from the group consisting of cyclic moeity; $C_{1-6}$ alkyl; $OR_{31}$ wherein, $R_{31}$ is hydrogen or $C_{1-6}$ alkyl; $SR_{32}$ wherein, $R_{32}$ is hydrogen or $C_{1-6}$ alkyl;
—NHC(O)$R_{33}$ wherein, $R_{33}$ is $C_{6-12}$ aryl, $C_{7-18}$ aralkyl or $C_{1-6}$ alkyl; —OC(O)$R_{34}$ wherein, $R_{34}$ is hydrogen, $C_{6-12}$ aryl, $C_{7-18}$ aralkyl, $C_{1-6}$ alkyl, —NHR$_{35}$ wherein, $R_{35}$ is hydrogen, $C_{6-12}$ aryl or $C_{1-6}$ alkyl; and NR$_6$R$_7$, wherein each of $R_6$ and $R_7$ is independently hydrogen or $C_{1-6}$ alkyl.

The invention also provides for pharmaceutically acceptable compositions comprising those compounds, for use in the treatment of pain.

The invention further provides the use of compound of formula (I) wherein that L is a $C_{1-2}$ alkyl chain which can be substituted with at least one substitutent selected from the group consisting of cyclic moeity; $C_{1-6}$ alkyl; $OR_{31}$ wherein, $R_{31}$ is hydrogen or $C_{1-6}$ alkyl; $SR_{32}$ wherein, $R_{32}$ is hydrogen or $C_{1-6}$ alkyl; —NHC(O)$R_{33}$ wherein, $R_{33}$ is $C_{6-12}$ aryl, $C_{7-18}$ aralkyl or $C_{1-6}$ alkyl; —OC(O)$R_{34}$ wherein, $R_{34}$ is hydrogen, $C_{6-12}$ aryl, $C_{7-18}$ aralkyl, $C_{1-6}$ alkyl, —NHR$_{35}$ wherein, $R_{35}$ is hydrogen, $C_{6-12}$ aryl or $C_{1-6}$ alkyl; and NR$_6$R$_7$, wherein each of $R_6$ and $R_7$ is independently hydrogen or $C_{1-6}$ alkyl; for the manufacture of peripheral analgesic for the treatment of pain.

DETAILED DESCRIPTION OF THE INVENTION

Z is preferably

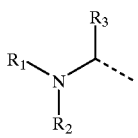

wherein each of $R_1$, $R_2$, and $R_3$ are as defined above.

$R_1$ is preferably hydrogen; NH$_2$C(=NH)—; or $C_{1-6}$ alkyl.
$R_1$ is more preferably hydrogen; NH$_2$C(=NH)—; or —CH$_3$.
$R_1$ is most preferably hydrogen.
$R_2$ is preferably hydrogen or —CH$_3$.
$R_2$ is more preferably hydrogen.
$R_3$ is preferably —CH$_2$—C$_6$H$_2$R$_8$R$_9$—, or —CH$_2$—HOC$_6$HR$_8$R$_9$, wherein each of $R_8$ and $R_9$ is independently —CH$_3$ or hydrogen.
$R_3$ is most preferably

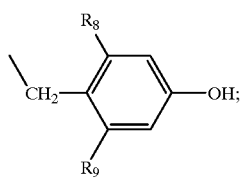

wherein $R_8$ and $R_9$ are as defined above.

$R_8$ and $R_9$ are preferably CH$_3$.
X is preferably —C(O)NH—; or —CH$_2$NH—.
X is more preferably —C(O)NH—.
L is preferably —(CH$_2$)$_{1-3}$—CHR$_{10}$—(CH$_2$)$_{1-3}$—, wherein $R_{10}$ is OH, or NH$_2$.
L is more preferably —(CH$_2$)—CHR$_{10}$—(CH$_2$)—, wherein $R_{10}$ is OH, or NH$_2$.
L is more preferably —(CH$_2$)—CHOH—(CH$_2$)—.
$R_4$ is preferably:
$C_{1-12}$ alkyl;

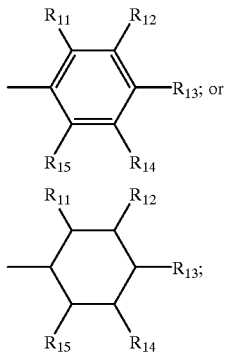

wherein each of $R_{11}$, $R_{12}$, $R_{13}$, $R_{14}$, and $R_{15}$ is independently CH$_3$, hydrogen, halogen, OH, SH, NH$_2$, or NO$_2$.
$R_4$ is more preferably: —CH$_3$; —C(CH$_3$)$_3$; —CH(CH$_3$)$_2$;

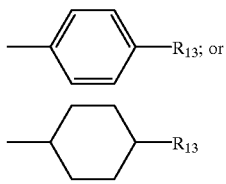

wherein $R_{13}$ is as defined above.

$R_4$ is most preferably selected from the group consisting of:

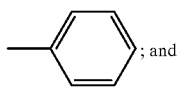; and

The compounds of the present invention are preferably selected from the group consisting of:

2-R-(2-Amino-3-(4-Hydroxy-2,6-dimethyl-phenyl)-propionyl)-1,2,3,4-tetrahydro-isoquinoline-3-S-carboxylic acid (2-hydroxy-3-phenyl-propyl)amide trifluoroacetic salt (racemic mixture) compound #1;

2-R-(2-Amino-3-(4-Hydroxy-2,6-dimethyl-phenyl)-propionyl)-1,2,3,4-tetrahydro-isoquinoline-3-S-carboxylic acid (2-hydroxy-3-phenyl-propyl)amide trifluoroacetic salt (fast isomer) compound #1A; 2-R-(2-Amino-3-(4-hydroxy-2,6-dimethyl-phenyl)-propionyl)-1,2,3,4-tetrahydro-isoquinoline-3-S-carboxylic acid (2-hydroxy-3-phenyl-propyl)amide trifluoroacetic salt (slow isomer) Compound #1B; 2-S-(2-Amino-3-(4-hydroxy-2,6-dimethyl-phenyl)-propionyl)-7-hydroxy1,2,3,4-tetrahydro-isoquinoline- 3-S-carboxylic acid (2-hydroxy-3-phenyl-propyl) amide trifluoroacetic salt (racemic mixture) compound #2; 2-(2-Guanidino-3-(4-hydroxy-2,6-dimethyl-phenyl)-propionyl)-1,2,3,4-tetrahydro-isoquinoline-3-S-carboxylic acid (2-R-hydroxy-3-phenyl-propyl)-amide ditrifloroacetic salt (racemic mixture) compound #3; 2-(2-Guanidino-3-(4-hydroxy-2,6-dimethyl-phenyl)-propionyl)-1,2,3,4-tetrahydro-isoquinoline-3-S-carboxylic acid (2-R-hydroxy-3-phenyl-propyl)-amide ditrifloroacetic salt (fast isomer) compound #3A; 2-(2-Guanidino-3-(4-hydroxy-2,6-dimethyl-phenyl)-propionyl)-1,2,3,4-tetrahydro-isoquinoline-3-S-carboxylic acid (2-R-hydroxy-3-phenyl-propyl)-amide ditrifloroacetic salt (slow isomer) compound #3B;

2-S-(2-Amino-3-(4-hydroxy-2,6-dimethyl-phenyl)-propionyl)-1,2,3,4-tetrahydro-isoquinoline-3-S-carboxylic acid (2-hydroxy-3-phenyl-propyl)amide trifluoroacetic salt (racemic mixture) of compound #4;

2-S-(2-Amino-3-(4-hydroxy-2,6-dimethyl-phenyl)-propionyl)-1,2,3,4-tetrahydro-isoquinoline-3-S-carboxylic acid (2-hydroxy-3-phenyl-propyl)amide trifluoroacetic salt (fast isomer) of compound # 4A;

2-S-(2-Amino-3-(4-hydroxy-2,6-dimethyl-phenyl)-propionyl)-1,2,3,4-tetrahydro-isoquinoline-3-S-carboxylic acid (2-hydroxy-3-phenyl-propyl)amide trifluoroacetic salt (slow isomer) Compound #4B;

S-2-(2-Amino-3-(hydroxy-phenyl)-S-1,2,3,4-tetrahydroisoquinoline-carboxylic acid (R-2-hydroxy-3-phenyl-propyl)-amide hydrochloride acid (racemic mixture) compound #8;

S-2-(2-Amino-3-(hydroxy-phenyl)-S-1,2,3,4-tetrahydroisoquinoline-carboxylic acid (R-2-hydroxy-3-phenyl-propyl)-amide hydrochloride acid (slow isomer) compound #8A;

2-S-Amino-3-(4-hydroxy-phenyl)-1-{3-(R-2-hydroxy-3-phenyl-propylamino)-methyl)-S-3,4-dihydro-1H-isoquinolin-2-yl}propan-1-one ditrifluoroacetic salt (fast isomer) compound #9A ;

2-(tyrosyl)-3S-(D-phenylalanamido methyl)-1,2,3,4-tetrahydro isoquinoline hydro chloride salt compound #10A;

2-(tyrosyl)-3S-phenylalanamido methyl)-1,2,3,4-tetrahydro isoquinoline hydro chloride salt compound #11A;

2-Tyrosyl-3S-tyrosamidomethyl-1,2,3,4-tetrahydroisoquinoline hydrochloride salt compound #12A;

2-Tyrosyl-3-benzoxycarboxamidomethyl-1,2,3,4-tetrahydroisoquinoline hydrochloride salt compound #13A;

trans-2-(3-(4-hydroxy-phenyl)-pyrrolidine-2-carbonyl-S-1,2,3,4-tetrahydroquinoline-3-carboxylic acid (R-2-hydroxy-3-phenyl-propyl)amide trifluoroacetic salt compound #14;

trans-2-(3-(4-hydroxy-phenyl)-pyrrolidine-2-carbonyl-S-1,2,3,4-tetrahydroquinoline-3-carboxylic acid (R-2-hydroxy-3-phenyl-propyl)amide trifluoroacetic salt (fast isomer) compound #14A; trans-2-(3-(4-hydroxy-phenyl)-pyrrolidine-2-carbonyl-S-1,2,3,4-tetrahydroquinoline-3-carboxylic acid (R-2-hydroxy-3-phenyl-propyl)amide trifluoroacetic salt (slow isomer) compound #14B;

and pharmaceutically acceptable derivatives thereof.

The compounds of the present invention are more preferably selected from the group consisting of:

2-R-(2-Amino-3-(4-hydroxy-2,6-dimethyl-phenyl)-propionyl)-1,2,3,4-tetrahydro-isoquinoline-3-S-carboxylic acid (2-hydroxy-3-phenyl-propyl)amide trifluoroacetic salt (slow isomer) Compound 1B; 2-S-(2-Amino-3-(4-hydroxy-2,6-dimethyl-phenyl)-propionyl)-7-hydroxy1,2,3,4-tetrahydro-isoquinoline-3-S-carboxylic acid (2-hydroxy-3-phenyl-propyl) amide trifluoroacetic salt (racemic mixture) compound #2; 2-(2-Guanidino-3-(4-hydroxy-2,6-dimethyl-phenyl)-propionyl)-1,2,3,4-tetrahydro-isoquinoline-3-S-carboxylic acid (2-R-hydroxy-3-phenyl-propyl)-amide ditrifloroacetic salt (fast isomer) compound #3A; 2-(2-Guanidino-3-(4-hydroxy-2,6-dimethyl-phenyl)-propionyl)-1,2,3,4-tetrahydro-isoquinoline-3-S-carboxylic acid (2-R-hydroxy-3-phenyl-propyl)-amide ditrifloroacetic salt (slow isomer) compound #3B;

2-S-(2-Amino-3-(4-hydroxy-2,6-dimethyl-phenyl)-propionyl)-1,2,3,4-tetrahydro-isoquinoline-3-S-carboxylic acid (2-hydroxy-3-phenyl-propyl)amide trifluoroacetic salt (fast isomer) of compound # 4A;

2-S-(2-Amino-3-(4-hydroxy-2,6-dimethyl-phenyl)-propionyl)-1,2,3,4-tetrahydro-isoquinoline-3-S-carboxylic acid (2-hydroxy-3-phenyl-propyl)amide trifluoroacetic salt (slow isomer) Compound #4B; and pharmaceutically acceptable derivatives thereof.

The compound of the present invention is most preferably 2-(2-Guanidino-3-(4-hydroxy-2,6-dimethyl-phenyl)-propionyl)-1,2,3,4-tetrahydro-isoquinoline-3-S-carboxylic acid (2-R-hydroxy-3-phenyl-propyl)-amide ditrifloroacetic salt (fast isomer) compound #3A; and pharmaceutically acceptable derivatives thereof.

There is also provided a pharmaceutically acceptable compositions comprising the analgesic compounds of the invention, for use in the treatment of pain.

In a further aspect of this invention, there is provided the use of an analgesic compound selected from the group consisting of:

(2-Amino-3-(4-Hydroxy-2,6-dimethyl-phenyl)-propionyl)-1,2,3,4-tetrahydro-isoquinoline-3-S-carboxylic acid (3-phenyl-propyl)amide trifluoroacetic salt (racemic mixture) compound #5;

2-(2-Amino-3-(4-Hydroxy-2,6-dimethyl-phenyl)-propionyl)-1,2,3,4-tetrahydro-isoquinoline-3-S-carboxylic acid (3-phenyl-propyl)amide trifluoroacetic salt (fast isomer) compound #5A;

2-(2-Amino-3-(4-Hydroxy-2,6-dimethyl-phenyl)-propionyl)-1,2,3,4-tetrahydro-isoquinoline-3-carboxylic acid (3-phenyl-propyl)amide trifluoroacetic salt compound #5B;

2-(2-Amino-3-(4-Hydroxy-2,6-dimethyl-phenyl)-propionyl)-1,2,3,4-tetrahydro-isoquinoline-3-S-carboxylic acid (3-phenyl-propyl)amide trifluoroacetic salt (racemic mixture) compound #6;

2-(2-Amino-3-(4-Hydroxy-2,6-dimethyl-phenyl)-propionyl)-1,2,3,4-tetrahydro-isoquinoline-3-S-carboxylic acid (3-phenyl-propyl)amide trifluoroacetic salt (fast isomer) compound #6A;

2-(2-Amino-3-(4-Hydroxy-2,6-dimethyl-phenyl)-propionyl)-1,2,3,4-tetrahydro-isoquinoline-3-S-carboxylic acid (3-phenyl-propyl)amide trifluoroacetic salt (slow isomer) compound #6B;

2-(2-Amino-3-(4-hydroxy-2,6-dimethyl-phenyl)-propionyl)-1,2,3,4-tetrahydro-isoquinoline-3-S-carboxylic acid (2-fluoro-(4-phenyl-ethyl)amide trifluoroacetic salt (racemic mixture) compound #7;

2-(2-Amino-3-(4-hydroxy-2,6-dimethyl-phenyl)-propionyl)-1,2,3,4-tetrahydro-isoquinoline-3-S-carboxylic acid (2-fluoro-(4-phenyl-ethyl)amide trifluoroacetic salt (fast isomer) compound #7A;

2-(2-Amino-3-(4-hydroxy-2,6-dimethyl-phenyl)-propionyl)-1,2,3,4-tetrahydro-isoquinoline-3-S-carboxylic acid (2-fluoro-(4-phenyl-ethyl)amide trifluoroacetic salt (slow isomer) compound #7B; and pharmaceutically acceptable derivatives thereof; for the manufacture of peripheral analgesic for the treatment of pain.

In a preferred embodiment, there is provided the use of an analgesic compound selected from the group consisting of:

2-(2-Amino-3-(4-Hydroxy-2,6-dimethyl-phenyl)-propionyl)-1,2,3,4-tetrahydro-isoquinoline-3-S-carboxylic acid (3-phenyl-propyl)amide trifluoroacetic salt (fast isomer) compound #5A; and 2-(2-Amino-3-(4-Hydroxy-2,6-dimethyl-phenyl)-propionyl)-1,2,3,4-tetrahydro-isoquinoline-3-carboxylic acid (3-phenyl-propyl)amide trifluoroacetic salt compound #5B;

2-(2-Amino-3-(4-hydroxy-2,6-dimethyl-phenyl)-propionyl)-1,2,3,4-tetrahydro-isoquinoline-3-S-carboxylic acid (2-fluoro-(4-phenyl-ethyl)amide trifluoroacetic salt (fast isomer) compound #7A;

and pharmaceutically acceptable derivatives thereof; for the manufacture of peripheral analgesic for the treatment of pain.

By "a pharmaceutically acceptable derivative" is meant any pharmaceutically acceptable salt, ester, or salt of such ester, of compound (I) or any other compound which, upon admistration to the recipient, is capable of providing (directly or indirectly) compound (I) or an active metabolite or residue thereof.

It will be appreciated by those skilled in the art that the compounds of formula (I), depending of the substitutents, may contain one or more chiral centres and thus exist in the form of many different isomers, optical isomers (i.e. enantiomers) and mixtures thereof including racemic mixtures. All such isomers, enantiomers and mixtures thereof including racemic mixtures are included within the scope of the invention As used in this application, the term "alkyl" represents a substituted (by a halogen, hydroxyl, amino, or $C_{6-20}$ aryl) or unsubstituted, straight chain, branched chain, or cyclic hydrocarbon moiety, wherein said straight chain, branched chain, or cyclic hydrocarbon moiety can be interrupted by one or more hetereoatoms (such as oxygen, nitrogen or sulfur).

The term "alkoxy" represents a substituted or unsubstituted alkyl group wherein the alkyl group is covalently bonded to an adjacent element through an oxygen atom (e.g., methoxy and ethoxy).

The term "alkoxyalkyl" represents an alkoxy group attached to the adjacent group by an alkyl group (e.g., methoxymethyl).

The term "aryl" represents a carbocyclic moiety which may be substituted or interrupted by at least one heteroatom (e.g., N, O, or S) and containing at least one benzenoid-type ring (e.g., phenyl and naphthyl).

The term "aralkyl" represents an aryl attached by the adjacent atom by an aklyl,( e.g. benzyl).

The term "acyl" refers to a radical derived from a carboxylic acid, substituted (by a halogen (F, Cl, Br, I), $C_{6-20}$ aryl or $C_{1-6}$ alkyl) or unsubstituted, by replacement of the —OH group. Like the acid to which it is related, an acyl radical may be aliphatic or aromatic, substituted (by a halogen, $C_{1-5}$ alkoxyalkyl, nitro or $O_2$) or unsubstituted, and whatever the structure of the rest of the molecule may be, the properties of the functional group remain essentially the same (e.g., acetyl, propionyl, isobutanoyl, pivaloyl, hexanoyl, trifluoroacetyl, chloroacetyl, and cyclohexanoyl).

By the term "cyclic moeity" is meant" an $C_{3-12}$ cycloalkyl interupted by at least one heteroatom such as O, N, or S. Examples of cyclic moeity include but are not limited to piperazine, morpholine, and thiomorpholine.

The terms "amino protecting groups and oxygen protecting groups" are well known in the field of peptide synthesis. Such amino protecting groups and oxygen protecting groups may be found in T. W Greene, *Protective Groups In Organic Synthesis*, (John Wiley & Sons, $2^e$ edition 1991). The appropriate protecting group for a particular synthetic scheme will depend on many factors, including the presence of other reactive functional groups and the reaction conditions desired for removal as well known by persons skilled in the art of peptide chemistry.

The term "$ED_{50}$" as shown in table 1 for the PBQ writhing assays is defined as the dose of drug which induces a 50% reduction in the number of writhes observed compared to the control. The term "$ED_{50}$" used in the hot-plate assays is defined as the dose of drug required to increase the latency of response 2-fold compared to controls and was determined by parallel-line probit analysis.

The term "$K_i$" is the binding inhibition constant.

Unless indicated otherwise, the amino acid present in the analgesic compounds of the present invention are in the natural L-configuration.

Throughout the application, the isomers are usually identified as slow and fast isomers depending of their retention time when analyzed by HPLC (high pressure liquid chromatography). This characterization method is well accepted in the art of peptide chemistry, see for example U.S. Pat. No. 4,599,325 issued on Jul. 8, 1986.

The term "residue" when applied to an amino acid, means a radical derived from the corresponding amino acid by removing the hydroxyl of the carboxyl group and one hydrogen from the amino group.

A number of compounds based on the general formula (I), have been prepared and evaluated as opioid receptor ligands and systemically acting analgesic agents. These compounds are listed in Table 1 along with their respective binding inhibition constants.

The present invention also provides for pharmaceutical compositions. Suitable compositions have a pharmaceutically effective amount of the compound of this invention, or pharmaceutically acceptable salts thereof, and a pharmaceutically acceptable carrier or adjuvant.

The present invention also provides for a method of treatment of pain in animals, such as mammals, including humans. The method comprises the steps of administering a pharmaceutically effective amount of a compound of formula (I) or a pharmaceutically acceptable derivative thereof, to the patient. A pharmaceutical composition as described above may also be used.

The following examples are used to better describe the invention. These examples are for the purpose of illustration only, and are not intended to limit the invention in any manner.

The opioid activity of the peptides was assessed in vitro using the guinea pig ileum (GPI) longitudinal muscle preparation and their antinociceptive activity was determined in vivo in PBQ induced writhing models (peripheral activity) and in the hot-plate test (central activity) in rodents. Antagonism of antinociception by the peripheral opioid antagonist N-methylnalorphine and by comparison of the activities in the writhing and hot-plate tests demonstrated that the analgesic effects were predominantly mediated in the periphery. Peripheral analgesia is shown by a high potency in the writhing test coupled with a low potency in the hot-plate test.

PBQ (phenyl-ρ-benzoquinone) induced writhing in mice is an assessment of both central and peripheral analgesia. For experimental protocol see Sigmund et al., *Proc. Soc. Exp. Biol. Med.*, 15, p. 729(1957) which is incorporated herein by reference. Central analgesia is determined by the inhibition of a hot-plate response in mice. For experimental protocol see G. Woolfe and A. Macdonald, *J. Pharmacol. Exp. Ther.*, 80, p.300 (1944) which is incorporated herein by reference. Assays measuring opioid receptor binding affinities for $\mu$ and $\delta$ receptors as well as GPI and MVD assays are determined through experimental protocol set out in Schiller et al., *Biophys. Res. Commun.*, 85, p.1322 (1975) incorporated herein by reference.

EXAMPLE 1

Radioligand Binding Assay

A. Membrane Preparation

Male Sprague-Dawley rats weighing between 350–450 g were sacrificed by inhalation of $CO_2$. The rats were decapitated and the brains minus cerebellum were removed and place in ice-cold saline solution and then homogenized in ice-cold 50 mM Tris buffer pH 7.4 (10 ml/brain). The membranes were centrifuged at 14000 rpm for 30 min. at 4° C. The pellets were re-suspended in approximately 6 ml/brain of ice-cold Tris buffer 50 mM pH 7.4 and stored at −78° C. until ready for use. Protein quantification of the brain homogenate was conducted according to protein assay kit purchased (Bio-Rad).

B. Radioligand Inhibition ($^3$H)-DAMGO and ($^3$H) DAGLE were used as radioligands for the $\mu$ and $\delta$ receptors, respectively. Radioligand 50 $\mu$l, membranes 100 $\mu$l and serially diluted test compound were incubated for 1 hr at 22° C. Non specific binding was determined using 500 fold excess of unlabeled ligand in the presence of tracer and membranes. Free ligand was separated from bound by filtration through Whatman GF/B paper (presoaked in polyethylenimine 1% aqueous solution) and rinsing with ice-cold 50 mM Tris pH 7.4 using a Brandel cell harvester. The filters were dried and radioactivity was counted in a 24 well microplate in the presence of 500 ml scintillant per well. Radioactivity was measured using a Wallac 1450 Microbeta counter.

Ki's for the various compounds were determined from the $IC_{50}$ according to the Cheng and Prusoff equation. Results of the binding assay are summarized in table 1.

The activity of the peptide compounds on $\mu$ receptors was determined using the Guinea Pig Ileum (GPI) assay (longitudinal muscle preparation) according to the procedures described in Schiller et al., *Biophys. Res. Commun.*, 85, p.1322 (1975). Activity results are summarized in table 1.

C) Writhing Assay

The test was performed on CD #1 male mice weighing between 18 and 22 g. The mice were weighed and marked. They were injected, by intra-peritoneal route, with 0.3 ml/20 g by weight with a solution of phenylquinone at 0.02%. The contortions which appeared during a 15 minute time period following the injection were counted. The phenylquinone was injected at time intervals of 5, 20 or 60 minutes after administration of the compound (or medium, or standard) by subcutaneous route.

The 0.02% phenylquinone solution was prepared in the following fashion. 20 mg of phenylquinone was dissolved in 5 ml ethanol 90% (sigma, reagent, alcohol). The dissolved phenylquinone was slowly added to 95 ml of distilled water continuously shaken and preheated (not boiled). The phenylquinone solution was left 2 hours before use, and at all times, protected from light. A new solution was prepared every day for the test.

Results of the assays are summarized below in table 1.

TABLE 1

| Compound # | $Ki^\mu$ (nM) | $Ki^\delta$ (nM) | $Ki^\kappa$ (nM) | $IC_{50}$ (nM) GPI | $ED_{50}$ (mg/kg) PBQ writhing |
|---|---|---|---|---|---|
| #3 | 2.03 ± 0.37 | 0.56 ± 0.09 | 276.6 ± 13.6 | | |
| #3B | 0.5 | | 164.3 ± 17.5 | 7.3 (2) | |
| #3A | 2.94 ± 0.73 | | 952 ± 122 | | 3.8 |
| #4B | 0.7 ± 0.27 | 0.1 ± 0.02 | 20.6 ± 0.5 | 13.8 | 16.6 |
| #6A | 0.11 ± 0.02 | 0.84 ± 0.08 | 49.6 ± 8.7 | 5.1 (1) | 2.4 |

EXAMPLE 2

In vitro stability of the compounds of the invention in rat whole blood (RWB) at 37° C. and in kidney brush border protease (KBBP) at 37° C.

a) In vitro stability in RWB at 37° C.

Procedure:

The compound was initially dissolved in water or in 10% methyl sulfoxide (DMSO)/water to make a stock solution of 10 mg/ml.

The stock solution was added to 15 ml of freshly harvested rat whole blood and incubated at 37° C.

Blanks were prepared without spiking with compounds in rat whole blood.

Aliquots were then taken at specific time intervals, centrifuged, and a fraction of the supernatant was extracted with acetonitrile or with a solution of acetonitrile and 10% acetic acid.

The solvent(s) was(were) removed by evaporation. The resulting residue was analyzed by HPLC.

The results are shown in Table 2

TABLE 2

| In vitro stability of the compounds of the invention in rat whole blood (RWB) at 37° C. | | | | |
|---|---|---|---|---|
| Compound # | % Extraction Efficiency | Metabolites in RWB | half life in RWB | Correlation Coefficient (r) |
| 4B | 66.7% ± 4.13 (n = 4) | none detected | >319 min. | 0.5580 |
| 4A | 93.3% ± 0.87 (n = 6) | none detected | >126 min. | 0.6738 |
| 5B | 88.0% ± 0.4 (n = 5) | none detected | >20 h | 0.1066 |
| 5A | 97.4% ± 2.7 (n = 5) | none detected | >24 h | 0.0409 | b) In vitro stability in KBBP at 37° C.

Procedure:

1.0 mg of the compounds were dissolved in 1 ml PBS pH 7.4 and 500 UL of proteases (1.14 mg of protein/ml) were added.

An initial aliquot was taken at time 0, and the reaction was immediately stopped by placing the sample in a bath of boiling water for 2 minutes (the other time intervals were 5, 15, 30, 60, 120, 1440 minutes).

Blank samples without compounds were also prepared.

The aliquoted samples were filtered on a micron 0.45 filter and the resulting sample were analyzed by HPLC.

The results are shown in table 3

TABLE 3

| In vitro stability in KBBP at 37° C. | | | |
|---|---|---|---|
| Compound # | Metabolites in KBBP | half life in KBBP | Correlation Coefficient (r) |
| 4B | none detected | >24 h | 0.0153 |
| 4A | 1 detected after 24 h (6%) | >24 h | 0.0486 |
| 5B | none detected | >24 h | 0.0777 |
| 5A | none detected | >24 h | 0.0017 |

EXAMPLE 3

Synthesis of 2-R-(2-Amino-3-(4-Hydroxy-2,6-dimethyl-phenyl)-propionyl)-1,2,3,4-tetrahydro-isoquinoline-3-S-carboxylic acid (2-hydroxy-3-phenyl-propyl)amide trifluoroacetic salt compound #1

Step 1

Synthesis of S-2-Chloro-3-phenyl-propionic acid

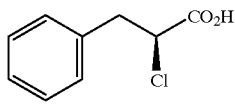

Sodium nitrite (3.34 g, 48.41 mmol) in 15 ML of water precooled at 0° C. was added dropwise to S-phenylalanine (5 g, 30.27 mmol) suspended in 80 ML of 5 N hydrochloric acid cooled with an ice/sodium chloride bath. After 5 h, the bath was removed and the reaction was allowed to stand overnight. While the mixture was stirred vigorously, solid sodium carbonate (6.05 g) was added carefully in small portions. The reaction mixture was extracted three times with ether. The combined ether portion was dried and evaporated. The residue was distilled at reduced pressure (5 mmHg) to give the desired product as oil (3.63 g, 65%).

$^1$H NMR (CDCl$_3$) δ: 9–10 (br , 1H), 7.31 (m, 5H), 4.51(dd, 1H, J=6.75 Hz, J=7.81 Hz), 3.64 (dd, 1H, J=14.10 Hz, J=6.75 Hz), 3.49 (dd, 1H, J=7.81 Hz, J=14.10 Hz).

STEP 2

Synthesis of S-2-Chloro-3-phenyl-propan-1-ol

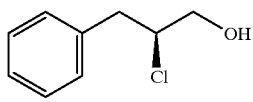

S-2-Chloro-3-phenyl-propionic acid (3.63 g, 19.66 mmol) in ether (10 ML) was added to lithium aluminum hydride (0.82 g, 21.63 mmol) in ether (20 ML) at 0° C. After 15 min., water (2 ML) was added. The precipitate was filtered off. The filtrate was evaporated. The residue was distilled under low pressure (5 mmHg) at 120° C. to give the desired product as oil (2.13 g, 64%).

$^1$H NMR (CDCl$_3$) δ: 7.30 (m, 5H), 4.23 (m, 1H), 3.81 (m, 1H), 3,71 (m, 1H), 3.61 (dd, 1H, J=14.42 Hz, J=6.93 Hz), 3.08 (1H, dd, J=14.42 Hz, J=7.49 Hz).

$^{13}$C NMR (CDCl$_3$) δ: 136, 128, 127, 126, 65, 64, 40.

IR (NaCl film) $v_{max}$: 3382, 2931, 1497, 1455, 1078, 1045 cm$^{-1}$.

STEP 3

Synthesis of R-2-Benzyl-oxirane

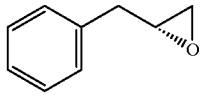

A solution of potasium hydroxide (4.45 g, 79.24 mmol) in water (10 ML) was added to S-2-chloro-3-phenyl-propan-1-ol (1.93 g, 11.32 mmol) in CH$_2$Cl$_2$ (15 ML) at 0° C. The solution was stirred overnight at r.t. The organic phase was separated, dried over MgSO$_4$, filtered, and evaporated. The residue was distilled under reduced pressure (5 mmHg) at 85° C. to yield the desired product as liquid (1.20 g, 79%).

$^1$H NMR (CDCl$_3$) δ: 7.30 ( m, 5H), 3.18 (m, 1H), 2.95 (dd, 1H), 2.84 (dd, 1H), 2.82 (dd, 1H), 2.57 (dd, 1H,).

$^{13}$C NMR (CDCl$_3$) δ: 134, 128, 127, 125, 52, 46, 38.

IR (NaCl film) $v_{max}$: 3029, 1497, 1455, 847, 818 cm$^{-1}$.

STEP 4

Synthesis of R-1-Amino-3-Phenyl-Propan-2-ol

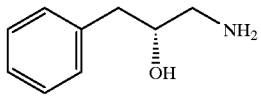

R-2-Benzyl-oxirane (5.02 g, 37.13 mmol) in aqueous amonium hydroxide (25%) (80 mL) was stirred for 72 hr at room temperature. Water was evaporated. The residue was distilled under reduced pressure (5 mm Hg) at 140° C. to yield the desired product as white solid (3.24 g, 58%).

$^1$H NMR (CDCl$_3$) δ: 7.30 (m, 5H), 3.73 (m, 1H), 2.78 (m, 3H), 2.56 (dd, 1H).

Step 5

Synthesis of S-3-(R-2-Hydroxy-3-phenyl-propylcarbamoyl)-3,4-dihydro-1H-isoquinoline-2-carboxylic acid tert-butyl ester

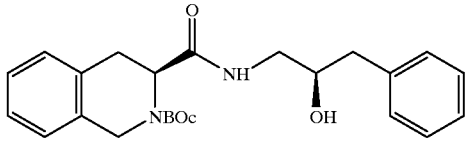

S-3,4-Dihydro-1H-isoquinoline-2,3-dicarboxylic acid 2-tert-butyl ester (0.50 g, 1.8 mmol) in dichloromethane (10 mL) was cooled to 0° C. (N$_2$ atmosphere), and triethylamine (0.18 g, 0.73 mmol) was added, then isobutyl chloroformate (0.25 g, 1.8 mmol) was added. The reaction mixture was stirred for 1 hr. R-1-Amino-3-phenyl-propan-2-ol (0.27 g, 1.8 mmol) was added. The reaction mixture was warmed to room temperature and stirred for another 1 hr. The mixture was diluted with dichloromethane, washed with 10% KHSO$_4$ aqueous solution, saturated NaHCO$_3$ aqueous solution and brine, then dried over MgSO$_4$, filtered, and concentrated. The residue was chromatographed on silica gel using ethyl acetate as eluant to provide the desired product as white solid (0.59 g, 80%).

¹H NMR (CDCl₃) δ: 7.2 (m, 9H), 4.8–4.5 (br, 2H), 4.0 (br, 1H), 3.80 (br, 1H), 3.1 (br, 4H), 2.5 (br, 2H), 1.4–1.3 (2 s, 9H).

LRMS: m/z MH⁺ 411.4, (C₂₄H₃₁N₂O₄)⁺ requires 411.5.

Step 6

Synthesis of S-1,2,3,4-tetrahydro-isoquinoline-3-carboxylic acid (R-2-hydroxy-3-phenyl-propyl) amide

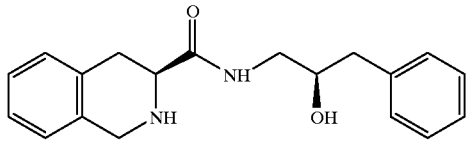

S-3- (R-2-Hydroxy-3-phenyl-propylcarbamoyl)-3,4-dihydro-1H-isoquinoline-2-carboxylic acid tert-butyl ester (0.55 g, 1.28 mmol) was dissolved in TFA/CH₂Cl₂ (1:1) (5 mL). The solution was stirred at room temperature for 1 hr. The solvent was evaporated. The residue was dissolved in ethyl acetate, washed with sat. NaHCO₃ aqueous solution and brine, dried with Na₂SO₄, and evaporated to yield the desired product as white solid (0.325 g, 83%)

¹H NMR (acetone) δ: 7.9 (br, 1H), 7.25–7.08 (m, 9H), 4.09 (d, 1H), 4.04 (d, 1H, J=16.3 Hz), 3.93 (m, 1H), 3.66 (dd, 1H, J=4.8 Hz, J=10.26 Hz), 3.37 (m 1H), 3.27 (m 1H), 3.15 (m, 1H), 2.89 (dd, 1H, J=10.5 Hz, J=16.2 Hz), 2.75 (m, 2H).

Step 7

Synthesis of {2-(4-Hydroxy-2,6-dimethyl-phenyl)-1-S-[3-R-(2-hydroxy-3-phenyl-propylcarbamoyl)-3,4-dihydro-1H-isoquinoline-2-carbonyl]-ethyl}-carbamic acid tert-butyl ester

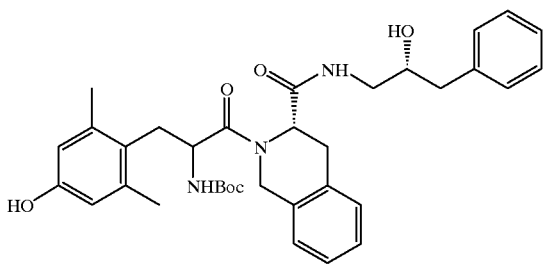

To a solution of 2-tert-butoxycarbonylamino-3-(4-hydroxy-2,6-dimethyl-phenyl)-propionic acid (0.54 g, 1.75 mmol), S-1,2,3,4-tetrahydro-isoquinoline-3-carboxylic acid [R-2-hydroxy-3-phenyl-propyl]-amide (0.62 g, 1.75 mmol) and HOBt.H₂O (0.29 g, 1.93 mmol) in DMF (5 mL) was added EDCI (0.37 g, 1.93 mmol) under nitrogen at 0° C. After stirring overnight at room temperature, the reaction mixture was diluted with ethyl acetate, washed with 10% KHSO₄ aqueous solution, saturated NaHCO₃ aqueous solution, and brine, then dried over MgSO₄, filtered, and concentrated. The residue was chromatographed on silica gel using ethyl acetate/dichloromethane (1:1) as eluant to provide the fast fraction as the desired product (0.40 g, 38%) and the slow fraction as its isomer (0.40 g, 38%).

¹H NMR (acetone) (partial) δ: 8.1 (s, 1H), 7.63 (br, 1H), 6.46 (2H), 2.18 (s, 6H), 1.39 (s, 9H).

Step 8

Synthesis of 2-R-(2-Amino-3-(4-Hydroxy-2,6-dimethyl-phenyl)-propionyl)-1,2,3,4-tetrahydro-isoquinoline-3-S-carboxylic acid (2-hydroxy-3-phenyl-propyl)amide trifluoroacetic salt (fast isomer) compound #1A

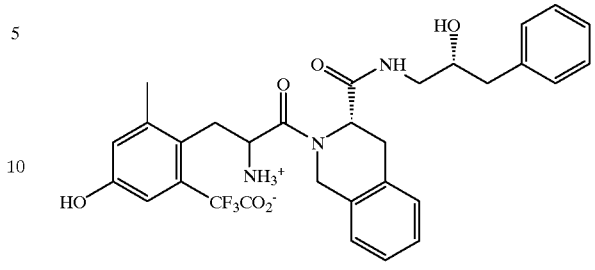

{2-(4-Hydroxy-2,6-dimethyl-phenyl)-1-S-[3-R-(2-hydroxy-3-phenyl-propylcarbamoyl)-3,4-dihydro-1H-isoquinoline-2-carbonyl]-ethyl}-carbamic acid tert-butyl ester (0.40 g, 0.66 mmol) was dissolved in TFA/CH₂Cl₂ (1:1) (5 mL). The solution was stirred at room temperature for 1 hr. The solvent was evaporated. The residue was purified by HPLC under gradient condition [0.1% (W/V) trifluoroacetic acid (TFA) in water/0.1% (W/V) TFA in acetonitrile (80/20 to 50/50, flow rate, 3 mL/min], followed by lyophilizing to yield the desire product as white powder (0.29 g, 71%).

¹H NMR (methanol) δ: 7.87 (t, 1H), 7.2–7.1 (m, 9 H0, 6.79 (d, 1H, J=7.2 Hz), 6.37 (s, 2H), 4.93 (t, 1H, J=5.0 Hz), 4.67 (dd, 1H, J=11.8 Hz, J=4.2 Hz), 4.47 (d, 1H, J=14.5 Hz), 3.74 (m, 1H), 3.67 (s, 1H), 3.37 (d, 1H, J=14.5 Hz), 3.26 (d, 1H, J=11.9 Hz), 3.15 (m, 4H), 2.83 (dd, 1H, J=5.7 Hz), 2.50 (m, 2H), 2.30 (s, 6H).

LRMS: m/z MH⁺ 502.6, [C₃₀H₃₆N₃O₄]⁺ requires 502.6

HPLC, purity 94%, rt=20.84

Step 9

Synthesis of 2-R-(2-Amino-3-(4-hydroxy-2,6-dimethyl-phenyl)-propionyl)-1,2,3,4-tetrahydro-isoquinoline-3-S-carboxylic acid (2-hydroxy-3-phenyl-propyl)amide trifluoroacetic salt (slow isomer) Compound 1B

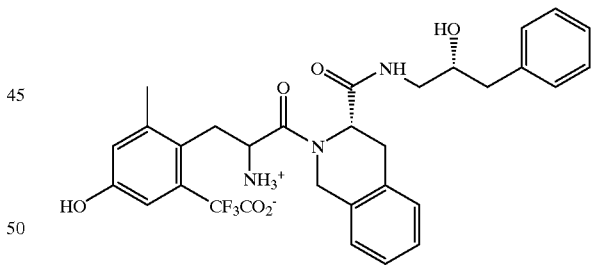

{2-(4-Hydroxy-2,6-dimethyl-phenyl)-1-S-[3-R-(2-hydroxy-3-phenyl-propylcarbamoyl)-3,4-dihydro-1H-isoquinoline-2-carbonyl]-ethyl}-carbamic acid tert-butyl ester (0.40 g, 0.66 mmol) was dissolved in TFA/CH₂Cl₂ (1:1) (5 mL). The solution was stirred at room temperature for 1 hr. The solvent was evaporated. The residue was purified by HPLC under gradient condition [0.1% (W/V) trifluoroacetic acid (TFA) in water/0.1% (W/V) TFA in acetonitrile (80/20 to 50/50, flow rate, 3 mL/min], followed by lyophilizing to yield the desire product as white powder (0.30 g, 73%).

¹H NMR (methanol) δ: 7.68 (t, 1H), 7.30–7.00 (m, 9H), 6.88 (d, 1H), 6.60 (s, 1H), 6.42 (s, 2H), 5.02 (t, ½H), 4.72 (d, 1H, J=12.7 Hz), 4.40 (d, ½H), 4.23 (dd, 1H, J=11.9 Hz, J=4.0 Hz), 3.80 (d, ½H), 3.70 (m, 1H), 3.25 (m, 1H), 3.15 (m, 3H), 2.82 (dd, 1H, J=4.4 Hz, J=15.81 Hz), 2.5–2.3 (m, 2H).

LRMS: m/z MH+ 502.6, [$C_{30}H_{36}N_3O_4$]+ requires 502.6

HPLC, purity 96%, rt=22.18

The following compounds were synthesized as generally described in example 3 except that the appropriate substitutions were made.

a) 2-S-(2-Amino-3-(4-hydroxy-2,6-dimethyl-phenyl)-propionyl)-7-hydroxy1,2,3,4-tetrahydro-isoquinoline-3-S-carboxylic acid (2-hydroxy-3-phenyl-propyl)amide trifluoroacetic salt (racemic mixture) compound #2

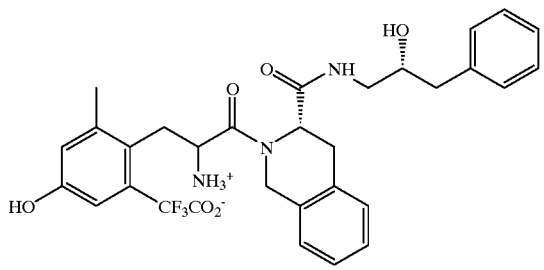

The residue was purified by HPLC under gradient condition [0.1% (W/V) trifluoroacetic acid (TFA) in water/0.1% (W/V) TFA in acetonitrile (80/20 to 50/50, flow rate, 3 mL/min], followed by lyophilizing to yield the desire product as white powder (0.125 g, 74%).

HPLC purity 97% b) 2-(2-Guanidino-3-(4-hydroxy-2,6-dimethyl-phenyl)-propionyl)-1,2,3,4-tetrahydro-isoquinoline-3-S-carboxylic acid (2-R-hydroxy-3-phenyl-propyl)-amide ditrifloroacetic salt (racemic mixture)compound #3

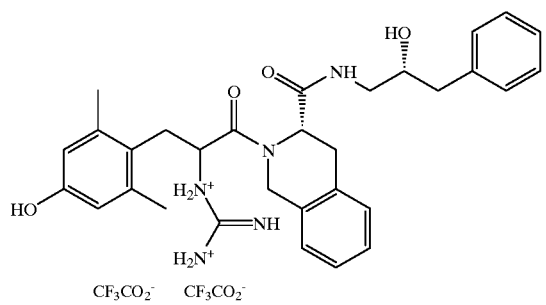

c)2-(2-Guanidino-3-(4-hydroxy-2,6-dimethyl-phenyl)-propionyl)-1,2,3,4-tetrahydro-isoquinoline-3-S-carboxylic acid (2-R-hydroxy-3-phenyl-propyl)-amide ditrifloroacetic salt compound #3A

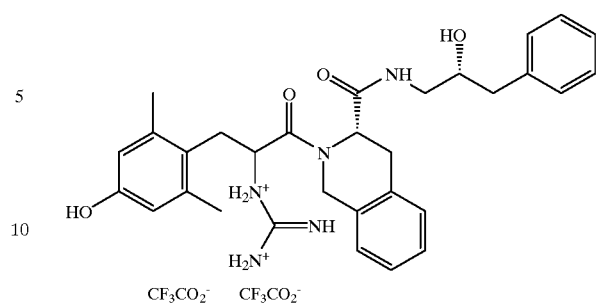

The residue was purified by HPLC under gradient condition [0.1% (W/V) trifluoroacetic acid (TFA) in water/0.1% (W/V) TFA in acetonitrile (80/20 to 50/50, flow rate, 3 mL/min], followed by lyophilizing to yield the desire product as white powder (0.087 g, 87%).

$^1$H NMR (methanol) δ: 7.91 (br, 1H), 7.51 (d, 1H, J=8.4 Hz), 7.25–7.00 (m, 9H), 6.41 (s, 2H), 5.02 (m, 1H), 4.91 (m, 1H), 4.70 (d, 1H, J=14.6 Hz), 3.96 (d, 1H, J=14.6 Hz), 3.76 (m, 1H), 3.15 (m, 4H), 3.05 (m, 2H), 2.52 (m, 2H).

HPLC purity 90%, rt=19.18 d) 2-(2-Guanidino-3-(4-hydroxy-2,6-dimethyl-phenyl)-propionyl)-1,2,3,4-tetrahydro-isoquinoline-3-S-carboxylic acid (2-R-hydroxy-3-phenyl-propyl)-amide ditrifloroacetic salt compound #3B

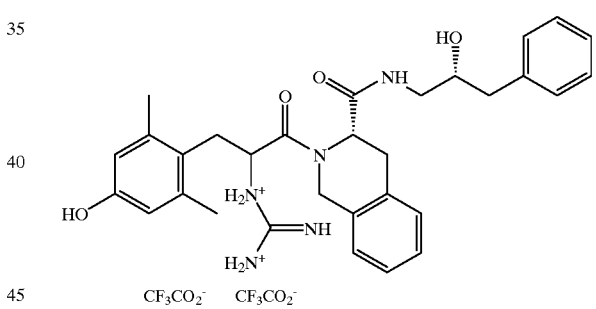

The residue was purified by HPLC under gradient condition [0.1% (W/V) trifluoroacetic acid (TFA) in water/0.1% (W/V) TFA in acetonitrile (80/20 to 50/50, flow rate, 3 mL/min], followed by lyophilizing to yield the desire product as white powder (0.078 g, 78%).

$^1$H NMR (methanol) δ: 7.88 (t, 1H) , 7.25–7.03 (m, 9H) , 6.47 (s, 2H), 4.68 (d, 1H, J=17.0 Hz), 4.49 (dd, 1H, J=4.3 Hz, J=11.16 Hz), 4.40 (d, 1H, J=17.0 Hz), 3.88 (t, 1H, J=4.4 Hz), 3.64 (m, 1H), 3.24 (m, 2H), 3.12 (t, 2H, J=5.8 Hz), 3.05 (dd, 1H, J=4.3 Hz, J=13.8 Hz), 2.87 (dd, 1H, J=3.7 Hz,, J=16.3 Hz), 2.30 (m, 2H), 2.21 (s, 6H).

HPLC, purity 87%, rt=19.57 e) 2-S-(2-Amino-3-(4-hydroxy-2,6-dimethyl-phenyl)-propionyl)-1,2,3,4-tetrahydro-isoquinoline-3-S-carboxylic acid (2-hydroxy-3-phenyl-propyl)amide trifluoroacetic salt (racemic mixture) compound #4

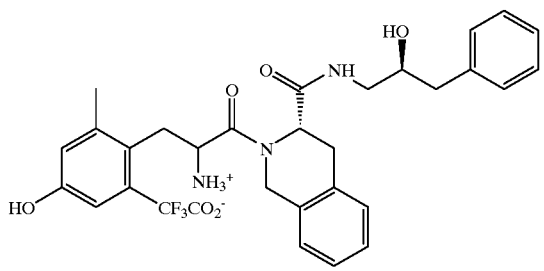

f) 2-S-(2-Amino-3-(4-hydroxy-2,6-dimethyl-phenyl)-propionyl)-1,2,3,4-tetrahydro-isoquinoline-3-S-carboxylic acid (2-hydroxy-3-phenyl-propyl)amide trifluoroacetic salt (fast isomer) of compound # 4A

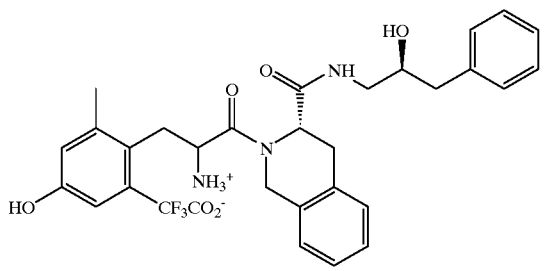

The residue was purified by HPLC under gradient condition [0.1% (W/V) trifluoroacetic acid (TFA) in water/0.1% (W/V) TFA in acetonitrile (80/20 to 50/50, flow rate, 3 mL/min], followed by lyophilizing to yield the desire product as white powder (0.040 g, 42%).

$^1$H NMR (methanol) δ: 7.87 (t, 1H), 7.2–7.1 (m, 9 H0, 6.79 (d, 1H, J=7.2 Hz), 6.37 (s, 2H), 4.93 (t, 1H, J=5.0 Hz), 4.67 (dd, 1H, J=11.8 Hz, J=4.2 Hz), 4.47 (d, 1H, J=14.5 Hz), 3.74 (m, 1H), 3.67 (s, 1H), 3.37 (d, 1H, J=14.5 Hz), 3.26 (d, 1H, J=11.9 Hz), 3.15 (m, 4H), 2.83 (dd, 1H, J=5.7 Hz), 2.50 (m, 2H), 2.30 (s, 6H).

LRMS: m/z MH$^+$ 502.6, $[C_{30}H_{36}N_3O_4]^+$ requires 502.6
HPLC purity 99%, rt=22.0 g) 2-S-(2-Amino-3-(4-hydroxy-2,6-dimethyl-phenyl)-propionyl)-1,2,3,4-tetrahydro-isoquinoline-3-S-carboxylic acid (2-hydroxy-3-phenyl-propyl)amide trifluoroacetic salt (slow isomer) Compound #4B

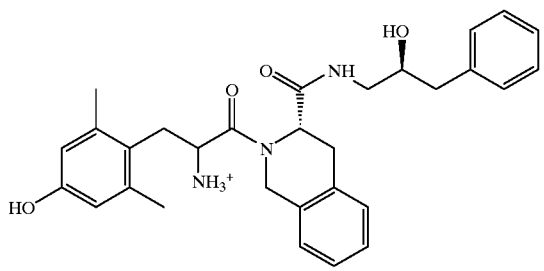

The residue was purified by HPLC under gradient condition [0.1% (W/V) trifluoroacetic acid (TFA) in water/0.1% (W/V) TFA in acetonitrile (80/20 to 50/50, flow rate, 3 mL/min], followed by lyophilizing to yield the desire product as white powder (0.043 g, 55%).

$^1$H NMR (methanol) δ: 7.68 (t, 1H), 7.30–7.00 (m, 9H), 6.88 (d, 1H), 6.60 (s, 1H), 6.42 (s, 2H), 5.02 (t, ½H), 4.72 (d, 1H, J=12.7 Hz), 4.40 (d, ½H), 4.23 (dd, 1H, J=11.9 Hz, J=4.0 Hz), 3.80 (d, ½H), 3.70 (m, 1H), 3.25 (m, 1H), 3.15 (m, 3H), 2.82 (dd, 1H, J=4.4 Hz, J=15.81 Hz), 2.5–2.3 (m, 2H).

LRMS: m/z MH$^+$ 502.6, $[C_{30}H_{36}N_3O_4]^+$ requires 502.6

HPLC purity 96%, rt=23.58 h) 2-(2-Amino-3-(4-Hydroxy-2,6-dimethyl-phenyl)-propionyl)-1,2,3,4-tetrahydro-isoquinoline-3-carboxylic acid (3-phenyl-propyl)amide trifluoroacetic salt (racemic mixture) compound #5

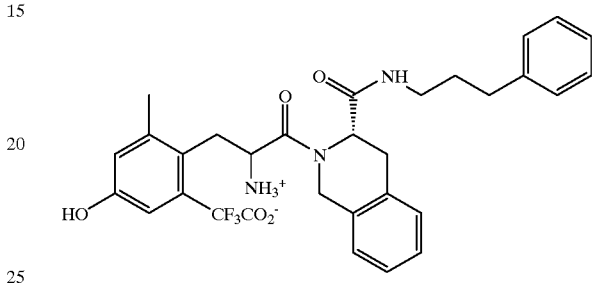

i) 2-(2-Amino-3-(4-Hydroxy-2,6-dimethyl-phenyl)-propionyl)-1,2,3,4-tetrahydro-isoquinoline-3-S-carboxylic acid (3-phenyl-propyl)amide trifluoroacetic salt (fast isomer) compound #5A

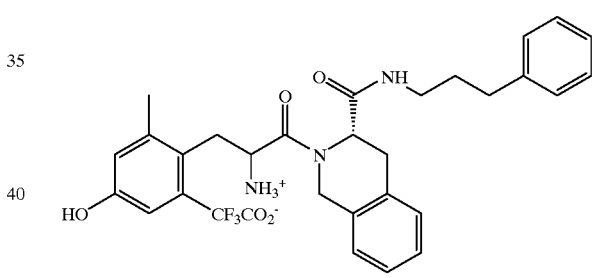

The residue was purified by HPLC under gradient condition [0.1% (W/V) trifluoroacetic acid (TFA) in water/0.1% (W/V) TFA in acetonitrile (80/20 to 50/50, flow rate, 3 mL/min], followed by lyophilizing to yield the desire product as white powder 0.074 g, 62%).

$^1$H NMR (methanol) δ: 7.94 (t, 1H), 7.23–7.04 (m, 9H), 6.79 (d, 1H, J=7.2 Hz), 6.37 (s, 2H), 4.92 (t, 1H, J=5.0 Hz), 4.64 (dd, 1H, J=11.8 Hz, J=4.3 Hz), 4.45 (d, 1H, J=14.6 Hz), 3.68 (d, 1H, J=14.6 Hz), 3.26 (d, 1H, J=12.0 Hz), 3.15 (m, 4H), 2.84 (dd, 1H, J=15.55 Hz, J=5.6 Hz), 2.41 (t, 2H, 7.5 Hz), 2.29 (s, 6H), 1.60 (m, 2H).

LRMS: m/z MH$^+$ 486.3, $[C_{30}H_{36}N_3O_3]^+$ requires 486.6

HPLC purity 95%, rt=19.77 j) 2-(2-Amino-3-(4-Hydroxy-2,6-dimethyl-phenyl)-propionyl)-1,2,3,4-tetrahydro-isoquinoline-3-carboxylic acid (3-phenyl-propyl)amide trifluoroacetic salt compound #5B

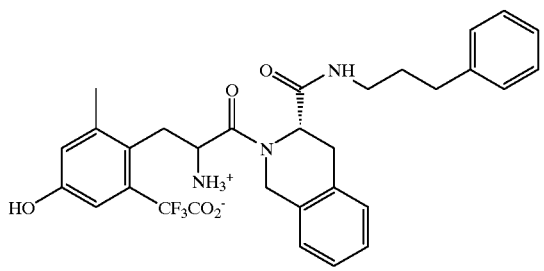

The residue was purified by HPLC under gradient condition [0.1% (W/V) trifluoroacetic acid (TFA) in water/0.1% (W/V) TFA in acetonitrile (80/20 to 50/50, flow rate, 3 mL/min], followed by lyophilizing to yield the desire product as white powder (0.074 g, 75%).

1H NMR (methanol) δ: 7.78 (t, 1H), 7.23–6.90 (m, 9H), 6.47 (s, 2H), 5.03 (t, ½H), 4.67 (d, 1H, J=16.9 Hz), 4.66 (m, ½H), 4.45 (d, ½H), 4.21 (dd, 1H, J=4.0 Hz, J=11.9 Hz), 3.80 (d, ½H), 3.72 (t, 1H, J=4.4 Hz), 3.15 (m, 2H), 2.83 (dd, 1H, J=16.04 Hz, J=3.6 Hz), 2.25 (m, 1H), 2.21 (s, 6H), 2.11 (dd, 1H, J=16.05 Hz, J=5.2 Hz), 1.53 (m, 2H).

LRMS: m/z MH⁺ 486.3, $[C_{30}H_{36}N_3O_3]^+$ requires 486.6
HPLC, purity 95%, rt=20.4 k) 2-(2-Amino-3-(4-Hydroxy-2,6-dimethyl-phenyl)-propionyl)-1,2,3,4-tetrahydro-isoquinoline-3-S-carboxylic acid (3-phenyl-propyl)amide trifluoroacetic salt (racemic mixture) compound #6

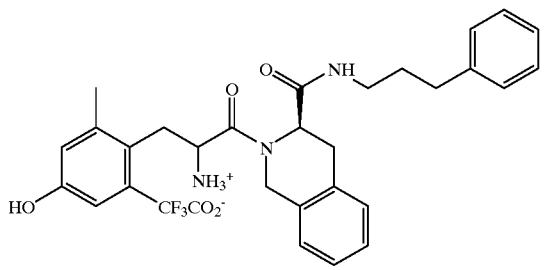

l) 2-(2-Amino-3-(4-Hydroxy-2,6-dimethyl-phenyl)-propionyl)-1,2,3,4-tetrahydro-isoquinoline-3-S-carboxylic acid (3-phenyl-propyl)amide trifluoroacetic salt (fast isomer) compound #6A

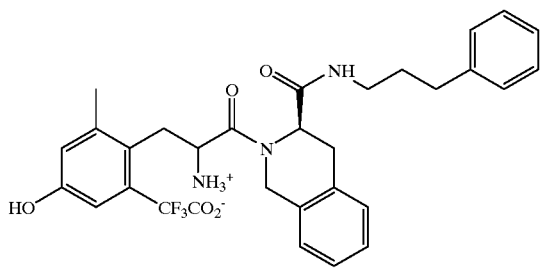

The residue was purified by HPLC under gradient condition [0.1% (W/V) trifluoroacetic acid (TFA) in water/0.1% (W/V) TFA in acetonitrile (80/20 to 50/50, flow rate, 3 mL/min], followed by lyophilizing to yield the desire product as white powder 0.074 g, 62%).

¹H NMR (methanol) δ: 7.94 (t, 1H), 7.23–7.04 (m, 9H), 6.79 (d, 1H, J=7.2 Hz), 6.37 (s, 2H), 4.92 (t, 1H, J=5.0 Hz), 4.64 (dd, 1H, J=11.8 Hz, J=4.3 Hz), 4.45 (d, 1H, J=14.6 Hz), 3.68 (d, 1H, J=14.6 Hz), 3.26 (d, 1H, J=12.0 Hz), 3.15 (m, 4H), 2.84 (dd, 1H, J=15.55 Hz, J=5.6 Hz), 2.41 (t, 2H, 7.5 Hz), 2.29 (s, 6H), 1.60 (m, 2H).

LRMS: m/z MH⁺ 486.3, $[C_{30}H_{36}N_3O_3]^+$ requires 486.6

HPLC purity 98%, rt=19.65 m) 2-(2-Amino-3-(4-Hydroxy-2,6-dimethyl-phenyl)-propionyl)-1,2,3,4-tetrahydro-isoquinoline-3-S-carboxylic acid (3-phenyl-propyl)amide trifluoroacetic salt (slow isomer)

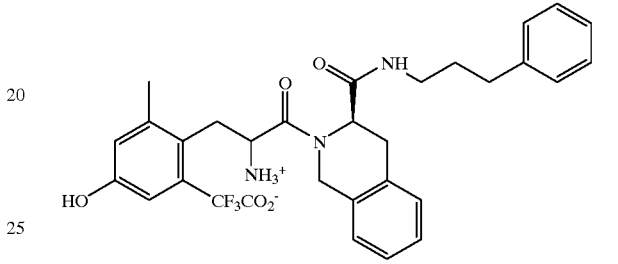

compound #6B

The residue was purified by HPLC under gradient condition [0.1% (W/V) trifluoroacetic acid (TFA) in water/0.1% (W/V) TFA in acetonitrile (80/20 to 50/50, flow rate, 3 mL/min], followed by lyophilizing to yield the desire product as white powder (0.074 g, 75%).

¹H NMR (methanol) δ: 7.78 (t, 1H), 7.23–6.90 (m, 9H), 6.47 (s, 2H), 5.03 (t, ½H), 4.67 (d, 1H, J=16.9 Hz), 4.66 (m, ½H), 4.45 (d, ½H), 4.21 (dd, 1H, J=4.0 Hz, J=11.9 Hz), 3.80 (d, ½H), 3.72 (t, 1H, J=4.4 Hz), 3.15 (m, 2H), 2.83 (dd, 1H, J=16.04 Hz, J=3.6 Hz), 2.25 (m, 1H), 2.21 (s, 6H), 2.11 (dd, 1H, J=16.05 Hz, J=5.2 Hz), 1.53 (m, 2H).

LRMS: m/z MH⁺ 486.3, $[C_{30}H_{36}N_3O_3]^+$ requires 486.6

HPLC, purity 98%, rt=20.11 n) 2-(2-Amino-3-(4-hydroxy-2,6-dimethyl-phenyl)-propionyl)-1,2,3,4-tetrahydro-isoquinoline-3-S-carboxylic acid (2-fluoro-(4-phenyl-ethyl)amide trifluoroacetic salt (racemic mixture) compound #7

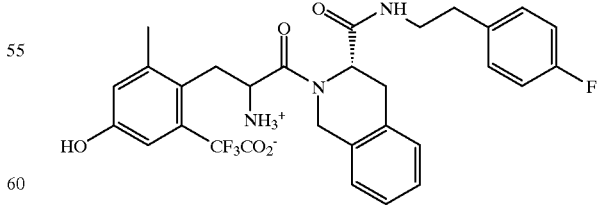

o) 2-(2-Amino-3-(4-hydroxy-2,6-dimethyl-phenyl)-propionyl)-1,2,3,4-tetrahydro-isoquinoline-3-S-carboxylic acid (2-fluoro-(4-phenyl-ethyl)amide trifluoroacetic salt compound #7A

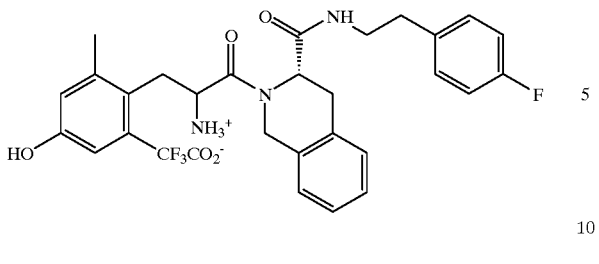

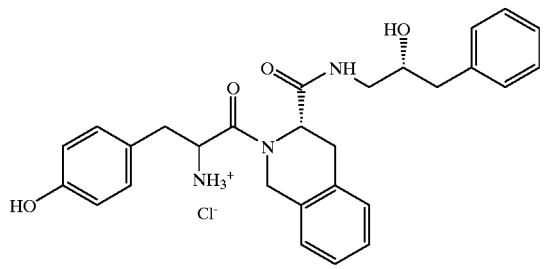

The residue was purified by HPLC under gradient condition [0.1% (W/V) trifluoroacetic acid (TFA) in water/0.1% (W/V) TFA in acetonitrile (80/20 to 50/50, flow rate, 3 mL/min], followed by lyophilizing to yield the desire product as white powder (0.106 g, 57%).

$^1$H NMR (methanol) δ: 7.98 (t, 1H), 7.17–6.77 (m, 8H), 6.35 (s, 2H), 4.92 (dd, 1H, J=4.1 Hz, J=5.6 Hz), 4.64 (dd, 1H, J=4.2 Hz, J=11.8 Hz), 4.40 (d, 1H, J=14.6 Hz), 3.37 (d, 1H, J=14.6 Hz), 3.25 (m, 3 H), 3.14 (dd, 1H, J=4.3 Hz, J=13.7 Hz), 3.05 (dd, 1H, J=4.0 Hz, J=15.6 Hz), 2.78 (dd, 1H, J=5.8 Hz, J=15.6 Hz), 2.58 (t, 1H, J=7.0 Hz), 2.28 (s, 6H).

HPLC, purity 99%, rt=18.62.

p) 2-(2-Amino-3-(4-hydroxy-2,6-dimethyl-phenyl)-propionyl)-1,2,3,4-tetrahydro-isoquinoline-3-S-carboxylic acid (2-fluoro-(4-phenyl-ethyl)amide trifluoroacetic salt compound #7B

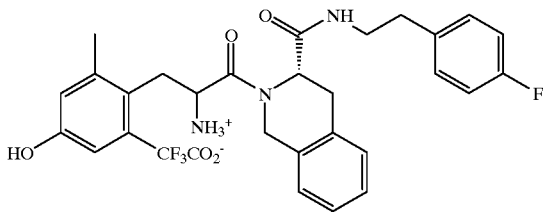

The residue was purified by HPLC under gradient condition [0.1% (W/V) trifluoroacetic acid (TFA) in water/0.1% (W/V) TFA in acetonitrile (80/20 to 50/50, flow rate, 3 mL/min], followed by lyophilizing to yield the desire product as white powder.

$^1$H NMR (methanol) δ: 7.84 (t, 1H), 7.25–7.05 (m, 4H), 6.98–6.88 (m, 5H), 6.61 (s, 1H), 6.43 (s, 2H), 5.05 (t, ½H, J=5.0 Hz), 4.70 (d, 1H, J=17.0 Hz), 4.69 (m, ½H), 4.44 (d, ½H, J=15.0 Hz), 4.40 (d, 1H, J=17.0 Hz), 4.19 (dd, 1H, J=4.0 Hz, J=11.97 Hz), 3.77 (d, 1H, J=15.0 Hz), 3.68 (t, 1H, J=4.5 Hz), 3.25 (m, 1H), 3.15 (m, 1H), 2.74 (dd, 1H, J=3.6 Hz, J=16.2 Hz), 2.55 (m, 2H), 2.17 (s, 6H), 2.04 (dd, 1H, J=16.1 Hz, J=5.2 Hz).

q) S-2-(2-Amino-3-(hydroxy-phenyl)-S-1,2,3,4-tetrahydroisoquinoline-carboxylic acid (R-2-hydroxy-3-phenyl-propyl)-amide hydrochloride acid (slow isomer) compound #8A LRMS, m/z MH$^+$ 474.4, [C$_{28}$H$_{32}$N$_3$O$_4$]$^+$ 474.6
HPLC, purity 98%, rt=45.69

EXAMPLE 4

2-S-Amino-3-(4-hydroxy-phenyl)-1-{3-(R-2-hydroxy-3-phenyl-propylamino)-methyl)-S-3,4-dihydro-1H-isoquinolin-2-yl}propan-1-one ditrifluoroacetic salt compound #9A Step 1

Synthesis of S-(1,2,3,4-Tetrahydro-Isoquinoline-3-yl)-Methanol

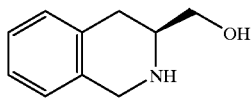

Borane-methyl sulfide complex (31.0 mmol) was added to the gently refluxing solution of S-1,2,3,4-tetrahydro-3-isoquinoline carboxylic acid (5.0 g, 28.22 mmol) and boron trifluoride ethorate (28.22 mmol) in THF (100 ML) under nitrogen. The solution was then refluxed overnight. The reaction mixture was cooled to 0° C. and quenched by slow addition of methanol (5 ML). the solvent was evaporated and the residue was dissolved in aqueous solution of sodium hydroxide (6 M) and reflux for 2 hr. the mixture was filtered through a cerite pad. The filtrate was extracted with chloroform, washed with brine, dried over MgSO$_4$ and evaporated. The crude product was recrystalized from CHCl$_3$ to give the desired product as crystals (4.0 g, 87%).

$^1$H NMR (CDCl$_3$) δ: 7.10 (4 H, m), 4.06 (2H, s), 3.77 (1H, dd, J=10.95 Hz, J=3.64 Hz), 3.52 (1H, dd, J=10.95 Hz, J=7.80 Hz), 3.08 (1H, m), 2.70 (1H, dd, J=16.27 Hz, J=4.26 Hz), 2.59 (1H, dd, J=16.27 Hz, J=10.85 Hz).

$^{13}$C NMR (CDCl$_3$) δ: 128.43, 125.34, 125.14, 124.98, 64.81, 54.18, 46.97, 30.05.

Step 2

Synthesis of S-3-Hydroxymethyl-3,4-dihydro-1H-isoquinoline-2-carboxylic acid benzyl ester

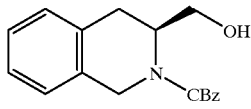

Benzylchloroformate (4.55 g, 26.69 mmol) was added to S-1,2,3,4-tetrahydroisoquinolin-3-yl)-methanol (3.96 g, 24.26 mmol) in water/dichloromethane (1:1, 100 ML). The solution was stirred vigorously for 3 h. The organic phase was washed with 10% aqueous KHSO$_4$, 5% aqueous NaHCO$_3$ and brine, dried over MgSO$_4$, filtered and evaporated. The residue was chromatographied using ethyl acetate:hexane (1:1) as eluant to yield the titled compound as oil (7.13 g, 99%).

$^1$H NMR (CDCl$_3$) δ: 7.38 (5H, m), 7.16 (4H, m), 5.21 (2H, dd), 4.80 (1H, dd), 4.77 (1H, br), 4.42 (1H, dd), 3.46–3.56 (2H, br), 3.06 (1H, dd, J=15.98 Hz, J=5.88 Hz), 2.69 (1H, dd, J=16.0 Hz, J=5.88 Hz), 2.66 (1H, br).

Step 3

Synthesis of S-3-Formyl-3,4-dihydro-1H-isoquinoline-2-carboxylic acid benzyl ester

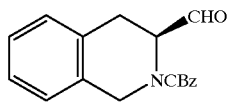

Periodinane (8.96 g, 21.20 mmol) was added to S-3-hydroxymethyl-3,4-dihydro-1H-isoquinoline-2-carboxylic acid benzyl ester (5.73 g, 19.27 mmol) in dichloromethane (150 ML) at r.t. The mixture was stirred for 20 min. The solution was washed with a mixture of 5% NaHCO$_3$ and 5% Na$_2$S$_2$O$_4$ aqueous solution, brine, dried over MgSO$_4$, and evaporated. The residue was purified by chromatography using ethyl acetate/hexane (1:1) as eluant to yield the desired product as oil (4.15 g, 73%).

$^1$H NMR (CDCl$_3$) δ: 9.54–9.48 (2 s, 1H), 7.46–7.09 (m, 9H), 5.27 (s, 1H), 5.21 (s, 1H), 4.94 (dd, ½H, J=6.4 Hz, J=3.5 Hz), 4.80 (d, 1H, J=16.4 Hz), 4.72 (t, ½H, J=4.7 Hz), 4.65 (d, 1H, J=16.5 Hz), 3.28 (dd, 1H, J=6.0 Hz, J=13.3 Hz), 3.10 (m 2H).

Step 4

Synthesis of S-3-[(R-2-Hydroxy-3-phenyl-propylamino)-methyl]-3,4-dihydro-1H-isoquinoline-2-carboxylic acid benzyl ester

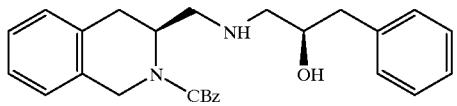

The mixture of S-3-formyl-3,4-dihydro-1H-isoquinoline-2-carboxylic acid benzyl ester (1.18 g, 3.99 mmol), R-1-amino-3-phenyl-propan-2-ol (0.60 g, 3.99 mmol), NaOAc (0.65 g, 7.98 mmol) and 4-Å molecular sieves (1.0 g) in methanol(20 ML) was stirred at r.t. for 3 h. NaBH$_3$CN (0.38 g, 5.99 mmol) was added. The mixture was stirred for another 3 h. 10% KHSO$_4$ aqueous solution was added to PH=4. The mixture was basified with saturated NaHCO$_3$ and most of the methanol was removed under reduced pressure. The mixture was extracted with ethyl acetate. The organic phase was washed with water and brine, dried over MgSO$_4$, filtered and concentrated. The residue was chromatographied using ethyl acetate as eluant to yield the titled compound as white solid (0.80 g, 46%)

$^1$H NMR (CDCl$_3$) δ: 7.14–7.41 (m, 14H), 5.24–5.16 (dd, 2H), 4.87 (br, 1H), 4.55 (br, 1H), 4.33 (br, 1H), 3.80 (br, 1H), 3.10 (br, 1H), 2.70 (m, 4H), 2.40 (m, 3H).

Step 5

Synthesis of S-3-{[tert-Butoxycarbonyl-(2-R-hydroxy-2-phenyl-propyl)-amino]-methyl}-3,4-dihydro-1H-isoquinoline-2-carboxylic acid benzyl ester

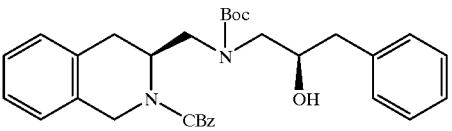

(Boc)$_2$O (0.44 g, 2.0 mmol) was added to a mixture of triethylamine (0.19 g, 1.83 mmol) and S-3-[(R-2-hydroxy-3-phenyl-propylamino)-methyl]-3,4-dihydro-1H-isoquinoline-2-carboxylic acid benzyl ester (0.79 g, 1.83 mmol) in DMF (5 ML). The reaction mixture was stirred at r.t. for 2 hr. The mixture was poured into water, extracted with ethyl acetate. The organic phase was washed with 10% KHSO$_4$ aqueous solution and brine, dried, and evaporated, The residue was purified by chromatography using ethyl acetate/hexane (3:7) as eluant to yield the desired product as oil (0.83 g, 85%).

Step 6

Synthesis of S-(R-2-Hydroxy-3-phenyl-propyl)-(1,2,3,4-tetrahydro-isoquinolin-3-ylmethyl)-carbamic tert-butyl ester

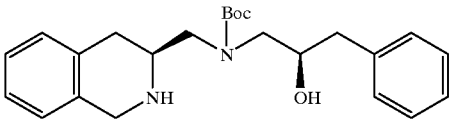

A solution of S-3-{[tert-butoxy carbonyl-(R-2-hydroxy-3-phenyl-propyl)-amino)-methyl]-3,4-dihydro-1H-isoquinoline-2-carboxylic acid benzyl ester (0.066 g, 0.14 mmol) in methanol (10 ML) containing HOAc (0.1 ML) was added 10% Pd-C (0.015 g) catalyst. The mixture was stirred under hydrogen for 1 hr. The catalyst was filtered off. The filtrate was evaporated. The residue was portioned between saturated NaHCO$_3$ aqueous solution and ethyl acetate. The organic phase was wished with brine, dried over MgSO$_4$, filtered and evaporated to yield the desired produce as white solid.(0.039 g, 71%)

$^1$H NMR (HOAc salt form) (acetone) δ: 7.99 (br, 2H), 7.28–7.07 (m, 9H), 4.15 (m, Br, 3H), 3.85 (m, 2H), 3.45 ( br, 1H), 3.25 (br, 1H), 2.95 (br, 1H), 2.75 (br, 4H).

LRMS, m/z MH$^+$ 397.2, [C$_{24}$H$_{33}$N$_2$O$_3$]$^+$ requires 397.5

Step 7

Synthesis of S-[1-(3-{[tert-Butoxycarbonyl-(R-2-hydroxy-3-phenyl-propyl)-amino]-methyl}-3,4-dihydro-1H-isoquinoline-2-S-carbonyl)-2-(4-tert-butoxy-phenyl)-ethyl]-carbamic acid tert-butyl ester

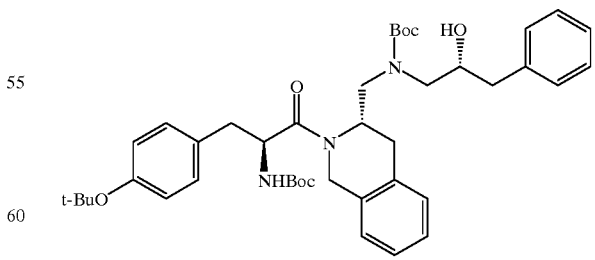

N-t-Boc-O-t-butyl-S-tyrosine (0.1 g, 0.26 mmol) in THF (5 mL) was cooled to 0° C. (N$_2$ atmosphere), and triethylamine (0.026 g, 0.26 mmol) was added, then isobutyl chloroformate (0.036 g, 0.26 mmol) was added. The reaction mixture was stirred for 1 hr. S-(R-2-Hydroxy-3-phenyl-propyl)-(1,2,3,4-tetrahydro-isoquinolin-3-ylmethyl)-carbamic tert-butyl ester (0.1 g, 0.26 mmol) was added. The reaction mixture was warmed to room temperature and stirred for another 1 hr. The mixture was diluted with dichloromethane, washed with 10% aqueous $KHSO_4$, saturated aqueous $NaHCO_3$, and brine, then dried over $MgSO_4$, filtered, and concentrated. The residue was chromatographed on silica gel using ethyl acetate as eluant to provide the desired product as white solid (0.14 g, 70%).

Step 8

Synthesis of 2-S-Amino-3-(4-hydroxy-phenyl)-1-{3-(R-2-hydroxy-3-phenyl-propylamino)-methyl)-S-3,4-dihydro-1H-isoquinolin-2-yl}propan-1-one ditrifluoroacetic salt (fast isomer) compound #9A

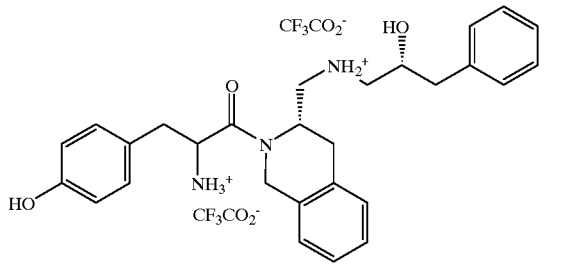

S-[1-(3-{[tert-Butoxycarbonyl-(R-2-hydroxy-3-phenyl-propyl)-amino]-methyl}-3,4-dihydro-1H-isoquinoline-2-S-carbonyl)-2-(4-tert-butoxy-phenyl)-ethyl]-carbamic acid tert-butyl ester (0.14 g, 0.23 mmol) was dissolved in 4N HCl in dioxane (5 ML). The solution was stirred at room temperature for 0.5 hr. The solvent was evaporated. The residue was dissolved in ethyl acetate, washed with water. The aqueous phase was dried by lyophilizing. The residue was purified by HPLC under gradient condition [0.1% (W/V) trifluoroacetic acid (TFA) in water/0.1% (W/V) TFA in acetonitrile (80/20 to 50/50, flow rate, 3 ML/min], followed by lyophilizing to yield the desire product as white powder (0.070 g, 58%).

LRMS, m/z $MH^+$ 460.1, $[C_{28}H_{33}N_3O_3]^+$ 460.6

HPLC, Purity 98%, rt=39.12

EXAMPLE 5

Synthesis of 2-(tyrosyl)-3S-(D-phenylalanamido methyl)-1,2,3,4-tetrahydro isoquinoline hydro chloride salt compound #10A Step 1

Synthesis of 3S-benzoxy carboxamidomethyl-1,2,3,4-tetrahydro isoquinoline

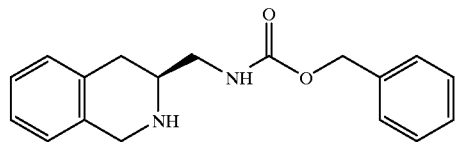

Diamine (87 mg, 0.54 mmol) in methylene chloride (5 ml) was treated with 4-dimethyl amino pyridine (2 mg) and carbobenzoxy imidazole (109 mg, 0.54 mmol). The mixture was stirred five days. The crude product was purified on preparative TLC to give desired product (120 mg). $^1$H NMR (400 MHz, $CDCl_3$), δ: 2.55 (dd, $J_1$=13.8 Hz, $J_2$=10.4 Hz, 1H), 2.78 (dd, $J_1$=13.8 Hz, $J_2$=3.0 Hz, 1H), 3.04 (m, 1H), 3.15 (m, 1H), 3.49 (m, 1H), 4.02 (s, 2H), 5.14 (s, 2H), 5.69 (s, 1H), 7.01–7.37 (m, 9H).

Step 2

Synthesis of 1S-t-butoxy carboxamido-2-(4-t-butoxy-phenyl)-(3-benzoxycarboxamido methyl-3,4-dihydro-1H-isoquinoline-2-yl)-ketone

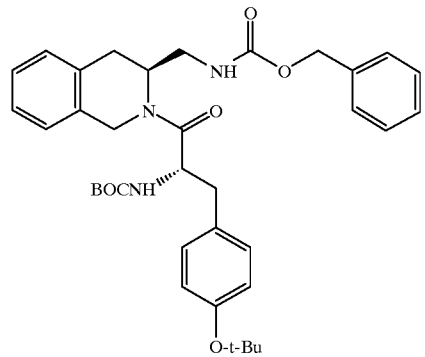

To an ice-cold DMF solution (4 ml) of mono-CBZ-protecte diamine (94 mg, 0.34 mmol), Boc-Tyr-(t-Bu)-OH and 1-hydroxybenzotriazole (48.4 mg, 0.358 mmol) was added 1,1'-cyclohexyl carbodimide (DCC, 73.8 mg, 0.358 mmol). The resulting mixture was stirred for 36 hours as it warmed to room temperature. Solvent was evaporated and the crude product was purified on silica gel (hexane:EtOAc= 2:1) to give desired product (60 mg).

$^1$H NMR (400 MHz, $CDCl_3$), δ: 1.24–1.37 (ms, 18H), 1.96 (dd, $J_1$=14.8 Hz, $J_2$=5.2 Hz, 1H), 2.35 and 2.70 (2d, $J_A$=14.8 Hz, $J_{B1}$=14.8 Hz, $J_{B2}$=1.7 Hz, 1H), 2.90–3.07 (m, 3H), 3.39 (m, 1H), 3.99 and 4.70 (2d, J=16.5 Hz, 1H), 4.25 (m, 1H), 4.94–5.10 and 5.20 (m, 3H), 5.45 and 5.46 (2d, J=8.6 Hz, 1H), 6.01 (m, 1H), 6.71 and 6.90 (2d, J=8.5 Hz, 2H), 7.06 (d, J=8.5 Hz, 2H), 7.08–7.34 (m, 9H).

Step 3

Synthesis of 2-(N-Boc-(O-t-bu))-tyrosyl-3S-aminomethyl-1,2,3,4-tetrahydro isoquinoline

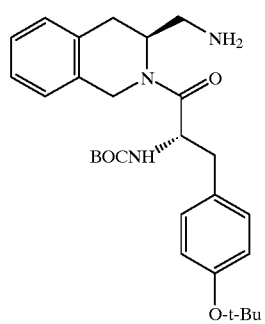

A methanolic solution of of 1S-t-butoxy carboxamido-2-(4-t-butoxy-phenyl)-(3-benzoxycarboxamidomethyl-3,4-dihydro-1H-isoquinoline-2-yl)-ketone (190 mg, 0.325 mmol) was hydrogenated for three hours under the catalysis of Pd/C (10%, 34.5 mg). It was filtered and the filtrate was evaporated to give a solid which was treated with NaOH (0.1 N) and extracted with $CHCl_3$. The organic layer was evaporated to dryness to give desired product (112 mg).

$^1$H NMR (400 MHz, $CDCl_3$), δ: 1.21, 1.26, 1.36, 1.39 (ms, 6×$CH_3$), 2.05 (dd, $J_1$=19 Hz, $J_2$=7 Hz, 1H), 2.44 (d,

J=19.0 Hz, 1H), 2.53 (m, 1H), 2.75, 2.85–3.00 (m, 4H), 3.73, 4.15, 4.65, 4.95 (4d, J=20 Hz, 2H), 3.97 (m, 1H), 4.76–5.06 (m, 2H), 4.44, 4.48 (2d, J=11.0 Hz, 1H), 6.68–7.20 (m, 8H).

Step 4

Synthesis of 2-(N-Boc-(O-t-bu)-tyrosyl)-3-(N-Boc-D-phenylalanamidomethyl)-1,2,3,4-tetrahydroisoquinoline

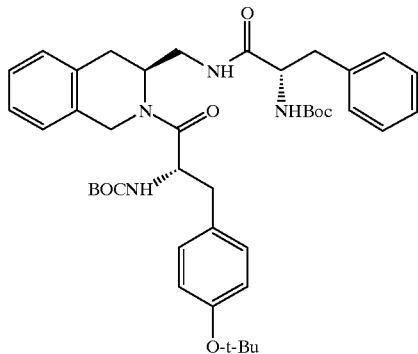

The free amine 2-(N-Boc-(O-t-bu))-tyrosyl-3S-aminomethyl-1,2,3,4-tetrahydro isoquinoline (56 mg, 0.117 mmol) was coupled to Boc-D-Phe (35.5 mg, 0.13 mmol) activated by isopropyl chloroformate (1.0 M solution, 0.135 ml, 0.135 mmol). After chromatography, the desired product was obtained (72 mg). $^1$H NMR (400 MHz, CDCl$_3$), δ: 1.29, 1.34, 1.36, 1.40, 1.41, 1.43 (ms, 27H), 2.07 (dd, J$_1$=17.1 Hz, J$_2$=4.8 Hz, 1H), 2.41 (d, J=17.1 Hz, 1H), 2.64 (btr, J=15.2 Hz, 1H), 2.86–3.21 (m, 4H), 3.96, 4.64 (2d, J=14.3 Hz, 1H), 4.25, 5.02 (2d, J=18.6 Hz, 2H), 4.03–5.15 (m, 5H), 5.24 (d, J=5.7 Hz, 1H), 5.39, 5.48 (2d, J=8 Hz, 1H), 6.84–7.32 (m, 13H).

Step 5

Synthesis of 2-(tyrosyl)-3S-(D-phenylalanamido methyl)-1,2,3,4-tetrahydro isoquinoline hydro chloride salt compound 5A

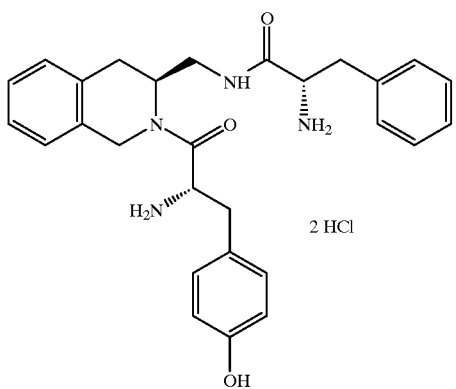

2-(N-Boc-(O-t-bu)-tyrosyl)-3-(N-Boc-D-phenylalanamidomethyl)-1,2,3,4-tetrahydroisoquinoline was deprotected by usual methods to yield the titled compound as the hydrochloride salt (22 mg).

$^1$H NMR (400 MHz, MeOH-d4), δ: 1.18 (dd, J$_1$=14.9 Hz, 4.0 Hz), 2.54 (d, J=14.9 Hz), 2.65 (dd, J$_1$=15 Hz, J$_2$=3.0 Hz), 2.81 (m) (all four sets of peaks, 2H), 3.00–3.25 (m, 4H), 3.92 (d, J=14.9 Hz), 4.00 (m) 4.06 (tr, J=8.9 Hz), 4.16 (tr, J=8.9 Hz), 4.43 (d, J=18.8 Hz), 4.63 (d, J=18.8 Hz), 4.67 (tr, J=7.9 Hz), 4.74 (d, J=18.8 Hz), 5.00 (m) (all nine sets of peaks, 7H), 6.72 (d, J=8.9 Hz), 6.90 (d, J=8.9 Hz), 7.09 (d, J=8.9 Hz), 7.17 (d, J=8.9 Hz), 7.03–7.70 (m) (all five sets of peaks, 13H), 8.04 (d, J=7.9 Hz), 8.48 (m), 8.60 (m) (all three sets of peaks, 1H).

The following compounds were synthesized as generally described in example 5, except that the appropriate substitutions were made.

a) 2-(tyrosyl)-3S-phenylalanamido methyl)-1,2,3,4-tetrahydro isoquinoline hydro chloride salt compound #11A

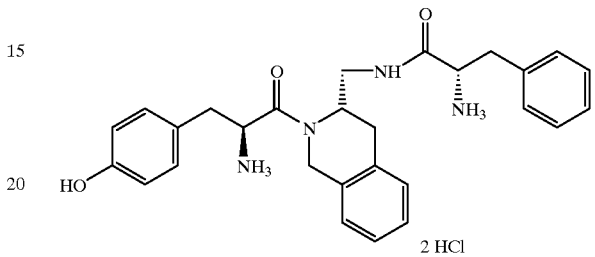

$^1$H NMR (400 MHz, MeOH-d4), δ: 1.85 (d, J=14.9 Hz, 1H), 1.93 (dd, J$_1$=14.9 Hz, J$_2$=5 Hz, 1H), 2.52, 2.76 (2m, 2H), 3.03–3.17 (m, 2H), 3.64 (m, 1H), 4.05 (m, 1H), 4.44 (d, J=18.8 Hz, 1H), 4.61 (d, J=18.8 Hz, 1H), 5.04 (m, 1H), 6.78–7.50 (m, 13H), 7.60–8.03 (2d, J=8.9 Hz, 1H), 8.27–8.47 (2m, 1H).

b) 2-Tyrosyl-3-benzoxycarboxamidomethyl-1,2,3,4-tetrahydroisoquinoline hydrochloride salt compound# 13A

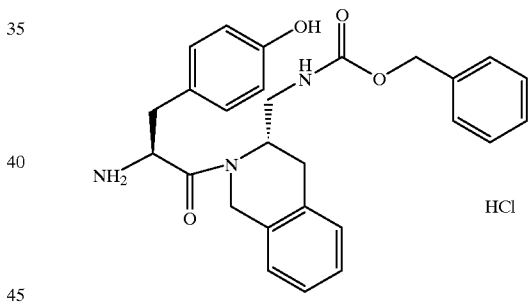

$^1$H NMR (400 MHz, MeOH-d4), δ: 2.16 (dd, J$_1$=14.6 Hz, J$_2$=4.9 Hz, 1H), 2.58 (dd, J$_1$=14.6 Hz, J$_2$=2 Hz, 1H), 2.62 (dd, J$_1$=12 Hz, J$_2$=9.8 Hz, 1H), 2.90–3.15 (m, 2H), 3.75 (bs, 1H), 4.44 (d, J=17.6 Hz, 1H), 4.66 (d, J=17.6 Hz, 1H), 4.30–4.76 (2d, J=15.6 Hz, 1H), 5.05 (tr. J=3.5 Hz, 1H), 5.10 (d, J=11.7 Hz, 1H), 5.23 (d, J=11.7 Hz, 1H), 6.67–7.40 (m, 13H).

EXAMPLE 6

Synthesis of 2-Tyrosyl-3S-tyrosamidomethyl-1,2,3,4-tetrahydroisoquinoline hydrochloride salt compound #12A Step 1

Synthesis of 3-(4-t-butoxy-phenyl)-2S-t-butoxy-carboxamido-1-[{3-(4-t-butoxy-phenyl)-2S-t-butoxy carboxamido propionamido methyl}-3,4-dihydro-1H-isoquinolin-2-yl]-propan-1-one

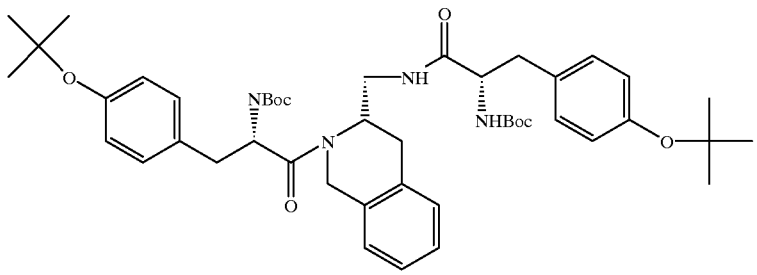

A solution of Boc-Tyr-(t-Bu)-OH (200 mg, 0.592 mmol) in THF (8 ml) was cooled to −10° C. and then treated with isobutylchloroformate (81.5 μl, 0.628 mmol) and subsequently with n-methyl morpholine (69 μl, 0.628 mmol). After being stirred for 15 minutes, a solution of diamine (67.5 mg, 2.287 mmol) in 2 ml of THF pre-treated with triethyl amine (79.9 μl, 0.574 mmol), was added. The resulting mixture was stirred for 2 days as it warmed to room temperature. The reaction mixture was evaporated to remove THF and redissolved in ether. The solution was then washed with dilute $K_2CO_3$ solution and then dried over sodium sulfate. Evaporation of solvent gave a crude product which was chromatographed to give product A (130 mg).

$^1$H NMR (400 MHz, $CDCl_3$), δ: 1.26–1.41 (m, 36H, 12×$CH_3$), 2.57–3.46 (m, 6H, 3×$CH_2$), 3.92 (br s, 1H, CH), 4.25–4.48 (m, 2H, $CH_2$), 4.25 (d, J=17.4 Hz, 1H), 4.60–4.70 and 4.85–4.96 (m, 1H), 4.83 (q, J=7.5 Hz, 1H), 5.12 (d, J=17.4, 1H), 5.25–5.35 (2×d, J=7.5 Hz, 1H), 5.81 (d, J=8.0 Hz, 1H), 6.80–7.20 (m, 12H).

Step 2

Synthesis of 2-Tyrosyl-3S-tyrosamidomethyl-1,2,3,4-tetrahydroisoquinoline hydrochloride salt

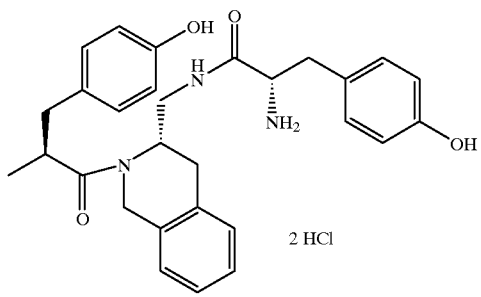

To a solution of 3-(4-t-butoxy-phenyl)-2S-t-butoxy-carboxamido-1-[{3-(4-t-butoxy-phenyl)-2S-t-butoxy carboxamido propionamido methyl}-3,4-dihydro-1H-isoquinolin-2-yl]-propan-1-one (130 mg, 0.162 mmol) in ether (5 ml) was passed a flow of HCl until a white suspension appeared. The resulting mixture was stirred for 1 hour as it warmed to room temperature. Solvent was evaporated to give a white solid which was purified on HPLC ($NH_4OAc$ buffer) to give desired product as a powder (61.3 mg).

$^1$H NMR (400 MHz, MeOH-d4), δ: 1.08 (dd, $J_1$=17.9 Hz, $J_2$=5.0 Hz, 1H), 2.16 (dd, $J_1$=17.9 Hz, $J_2$=2Hz, 1H), 2.75–3.04 (m, 6H), 3.54 (tr, J=6.0 Hz, 1H), 4.03 (q, J=7.0 Hz, 1H), 4.28 (d, J=18.9 Hz, 1H), 4.53 (dd, $J_1$=6.0 Hz, $J_2$=9.0 Hz, 1H), 4.75 (d, J=18.9 Hz, 1H), 6.68 (d, J=9.4 Hz, 2H), 6.75 (d, J=9.4 Hz, 2H), 7.02 (d, J=9.4 Hz, 2H), 7.03 (d, J=9.4 Hz, 2H), 6.95–7.20 (m, 5H).

EXAMPLE 7

Synthesis of trans-2-(3-(4-hydroxy-phenyl)-pyrrolidine-2-carbonyl-S-1,2,3,4-tetrahydroquinoline-3-carboxylic acid (R-2-hydroxy-3-phenyl-propyl)amide trifluoroacetic salt compound #14

Step 1

Synthesis of trans-2-(3S-{[tert-butoxycarbonyl(2R-hydroxy-3-phenyl-propyl)-amino]-methyl-3,4-dihydro-1H-isoquinoline-2-S-carbonyl)-3-(4-hydroxy-phenyl)-pyrrolidine-1-carboxylic acid tert-butyl ester

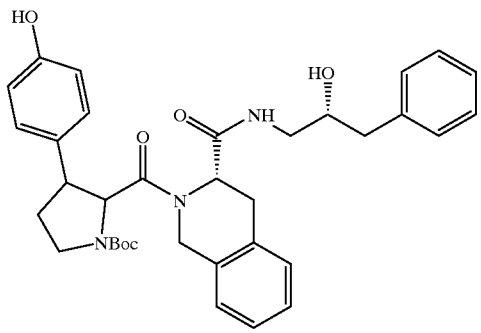

To a solution of trans 3-(4-hydroxy-phenyl)-pyrrolidine-1,2-dicarboxylic acid 1-tert-butyl ester which is produced as described in J.Med. Chem. 1994, 37, 4371–4383 (0.10 g, 0.35 mmol), 1,2,3,4-tetrahydro-isoquinoline-3S-carboxylic acid[2R-hydroxy-3-phenyl-propyl]-amide (0.12 g, 0.35 mmol) and DIEA (0.090 g, 0.70 mmol) in DMF (5 mL) was added PyBrOP (0.16 g, 0.35 mmol) under nitrogen at 0° C. After stirring overnight at ambient temperature, the reaction mixture was diluted with ethyl acetate, washed with 10% aqueous $KHSO_4$, saturated aqueous $NaHCO_3$, and brine, then dried over $MgSO_4$, filtered, and concentrated. The residue was chromatographed on silica gel using ethyl acetate/hexane (3:7) as eluant to provide the fast fraction as the TLC fast isomer (0.69 g, 36%) and the slow fraction as the TLC slow isomer (0.75 g, 39%).

$^1$H NMR (400 MHz, Bruker, acetone-d6) (TLC slow isomer)δ: 8.35 (s, 1H), 7.48 (br, 1H), 7.20–6.70 (m, 13H), 5.32 (dd, 1H, J=1.7 Hz, J=6.5 Hz), 4.83 (d, 1H, J=15.3 Hz), 4.76 (d, 1H, J=8.7 Hz), 4.10 (m, 1H), 3.80 (m, 2H), 3.60–3.40 (m, 3H), 3.25 (m, 1H), 2.85 (m, 1H), 2.76 (dd, 1H, J=14.5 Hz, J=5.3 Hz), 2.52 (dd, 1H, J=13.5 Hz, J=8.2 Hz), 2.25 (m, 2H), 1.43 (s, 9H).

$^1$H NMR (400 MHz, Bruker, acetone-d6) (TLC fast isomer)δ: 8.53 (m, 1H), 7.94 (br, 1H), 7.30–6.70 (, 13H), 5.00 (m, 1H), 4.80–4.68 (m, 1H), 4.25 (m, 1H), 3.75 (m, 2H), 3.50 (m, 2H), 3.45 (m, 1H), 3.25 (m, 1H), 3.10 (m, 4H), 2.55 (m, 2H), 2.20 (m, 2H), 1.44 (2s, 9H).

Step 2

Synthesis of trans-2-(3-(4-hydroxy-phenyl)-pyrrolidine-2-carbonyl-S-1,2,3,4-tetrahydroquinoline-3-carboxylic acid (R-2-hydroxy-3-phenyl-propyl)amide trifluoroacetic salt (fast isomer) compound #14A

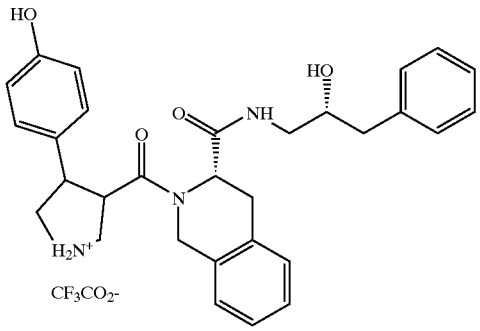

trans-2-(3S-{[tert-Butoxycarbonyl-(2R-hydroxy-3-phenyl-propyl)-amino]-methyl-3,4-dihydro-1H-isoquinoline-2-carbonyl)-3-(4-hydroxy-phenyl)-pyrrolidine-1-carboxylic acid tert-butyl ester (0.069 g, 0.12 mmol) was dissolved in 4N HCl in dioxane (5 mL). The solution was stirred at room temperature for 0.5 hr. The solvent was evaporated. The residue was purified by HPLC on a Vydac C18 column under gradient condition [0.1% (W/V) trifluoroacetic acid (TFA) in water/0.1% (W/V) TFA in acetonitrile (80/20 to 50/50, flow rate, 3 mL/min], followed by lyophilizing to yield the desire product as white powder (0.027 g, 38%).

LRMS, m/z MH$^+$ 500.6, [C$_{30}$H$_{34}$N$_3$O$_4$]$^+$ requires 500.6

Step 2

Synthesis of trans-2-(3-(4-hydroxy-phenyl)-pyrrolidine-2-carbonyl-S-1,2,3,4-tetrahydroquinoline-3-carboxylic acid (R-2-hydroxy-3-phenyl-propyl)amide trifluoroacetic salt (slow isomer) compound #14B

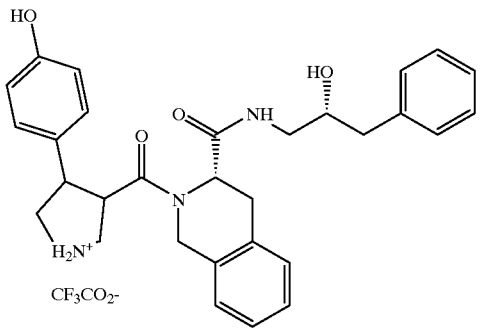

Trans-2-(3S-{[tert-Butoxycarbonyl-(2R-hydroxy-3-phenyl-propyl)-amino]-methyl-3,4-dihydro-1H-isoquinoline-2-carbonyl)-3-(4-hydroxy-phenyl)-pyrrolidine-1-carboxylic acid tert-butyl ester (TLC fast isomer) (0.069 g, 0.12 mmol) was dissolved in 4N HCl in dioxane (5 mL). The solution was stirred at room temperature for 0.5 hr. The solvent was evaporated. The residue was purified by HPLC on a Vydac C18 column under gradient condition [0.1% (W/V) trifluoroacetic acid (TFA) in water/0.1% (W/V) TFA in acetonitrile (80/20 to 50/50, flow rate, 3 mL/min], followed by lyophilizing to yield the desire product as white powder (0.028 g, 38%).

LRMS, m/z MH$^+$ 500.5, [C$_{30}$H$_{34}$N$_3$O$_4$]$^+$ requires 500.6

We claim:

1. An analgesic compound of formula (I):

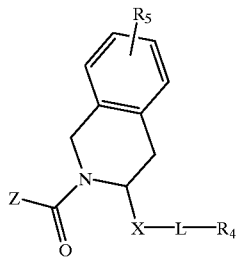

(I)

wherein;

Z is

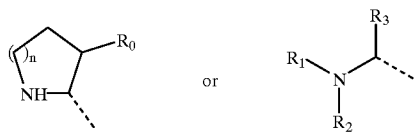

wherein, n is 1 or 2, and R$_0$ is C$_{6-12}$ aryl or C$_{7-8}$ aralkyl; or

R$_1$ is selected from the group consisting of hydrogen; —NH—C$_{1-6}$ alkyl; C$_{1-6}$ alkyl; C$_{6-12}$ aryl; C$_{7-18}$ aralkyl; arginyl; and R$_{30}$NHC(=NH)—, wherein R$_{30}$ is hydrogen, C$_{6-12}$ aryl, C$_{7-18}$ aralkyl, or C$_{1-6}$ alkyl;

R$_2$ is hydrogen; C$_{1-6}$ alkyl; or OH;

R$_3$ is C$_{6-12}$ aryl; C$_{7-18}$ aralkyl; —CH$_2$—C$_6$H$_3$R$_8$R$_9$; or —CH$_2$—OHC$_6$H$_2$R$_8$R$_9$, wherein each of R$_8$ and R$_9$ is independently CH$_3$ or hydrogen;

R$_4$ is C$_{6-12}$ aryl; C$_{7-18}$ aralkyl; C$_{1-12}$ alkyl; an unsubstituted cyclohexyl or a cyclohexyl substituted at one or more positions with CH$_3$, halogen, OH, SH, NH$_2$, or NO$_2$, wherein there is no more than one substituent per position and the 1 position does not have a substituent;

R$_5$ is C$_{1-6}$ alkyl; hydrogen; OH; halogen; SH; NO$_2$; NH$_2$; —NH—C$_{1-6}$ alkyl; NH$_2$C(=NH —; NH$_2$C(=NH)—NH—; COOR$_{31}$, wherein, R$_{31}$ is hydrogen, or C$_{1-6}$ alkyl;

X is CH$_2$NHC(O)—; CH$_2$NHC(O)O; —C(O)NH—; or CH$_2$NH—; and

L is a C$_{1-12}$ alkylene chain which can be substituted with at least one substituent selected from the group consisting of; a C$_3$–C$_{12}$ heterocycle containing at least one heteroatom selected from the group consisting of O, N, and S; C$_{1-6}$ alkyl; OR$_{31}$ wherein, R$_{31}$ is hydrogen or C$_{1-6}$ alkyl; SR$_{32}$ wherein, R$_{32}$ is hydrogen or C$_{1-6}$ alkyl; —NHC(O)R$_{33}$ wherein, R$_{33}$ is C$_{6-12}$ aryl, C$_{7-18}$ aralkyl or C$_{1-6}$ alkyl; —OC(O)R$_{34}$ wherein, R$_{34}$ is hydrogen, C$_{6-12}$ aryl, C$_{7-18}$ aralkyl, C$_{1-6}$ alkyl, —NHR$_{35}$ wherein, R$_{35}$ is hydrogen, C$_{6-12}$ aryl or C$_{1-6}$ alkyl; and NR$_6$R7, wherein each of R$_6$ and R$_7$ is independently hydrogen or C$_{1-6}$ alkyl; with the proviso that when R$_5$ is hydrogen, Z is

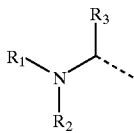

and X is —C(O)NH—, or —CH$_2$NH—, then L is a C$_{1-12}$ alkyl chain substituted with at least one substituent selected from the group consisting of a C$_3$–C$_{12}$ heterocycle containing at least one heteroatom selected from the group consisting of O, N, and S; C$_{1-6}$ alkyl; OR$_{31}$ wherein, R$_{31}$ is hydrogen or C$_{1-6}$ alkyl; SR$_{32}$ wherein, R$_{32}$ is hydrogen or C$_{1-6}$ alkyl; —NHC(O)R$_{33}$ wherein, R$_{33}$ is C$_{6-12}$ aryl, C$_{7-18}$ aralkyl or C$_{1-6}$ alkyl; —OC(O)R$_{34}$ wherein, R$_{34}$ is hydrogen, C$_{6-12}$ aryl, C$_{7-18}$ aralkyl, C$_{1-6}$ alkyl, —NHR$_{35}$ wherein, R$_{35}$ is hydrogen, C$_{6-12}$ aryl or C$_{1-6}$ alkyl; and NR$_6$R$_7$, wherein each of R$_6$ and R$_7$ is independently hydrogen or C$_{1-6}$ alkyl.

2. An analgesic compound according to claim 1 wherein; z is

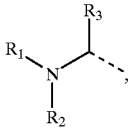

wherein each of R$_1$, R$_2$, and R$_3$ are as defined in claim 1.

3. An analgesic compound according to claim 1 wherein;
R$_1$ is hydrogen; NH$_2$C(=NH)—; or C$_{1-6}$ alkyl;
R$_2$ is hydrogen or —CH$_3$; and
R$_3$ is selected from the group consisting of:
—CH$_2$—C$_6$H$_3$R$_8$R$_9$; or —CH$_2$—OHC$_6$H$_2$R$_8$R$_9$, wherein each of R$_8$ and R$_9$ is independently —CH$_3$ or hydrogen.

4. An analgesic compound according to claim 3 wherein;
R$_1$ is hydrogen; NH$_2$C(=NH)—; or —CH$_3$;
R$_2$ is hydrogen; and

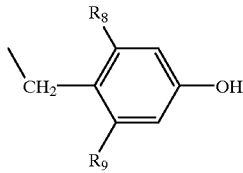

R$_3$ is wherein each of R$_8$ and R$_9$ is independently —CH$_3$ or hydrogen.

5. An analgesic compound according to claim 4 wherein;
R$_8$ and R$_9$ are CH$_3$.

6. An analgesic compound according to anyone of claims 1 to 5 wherein;
X is —C(O)NH—; or —CH$_2$NH—.

7. An analgesic compound according to anyone of claims 1 to 5 wherein X is —C(O)NH—.

8. An analgesic compound according to anyone of claims 1 to 5 wherein L is —(CH$_2$)$_{1-3}$—CHR$_{10}$—(CH$_2$)$_{1-3}$—, wherein R$_{10}$ is OH, or NH$_2$.

9. An analgesic compound according to anyone of claims 1 to 5 wherein L is —(CH$_2$)—CHR$_{10}$—(CH$_2$)—, wherein R$_{10}$ is OH, or NH$_2$.

10. An analgesic compound according to anyone of claims 1 to 5 wherein L is more preferably —(CH$_2$)—CHOH—(CH$_2$)—.

11. An analgesic compound according to anyone of claims 1 to 5 wherein:
R$_4$ is selected from the group consisting of:
C$_{1-12}$ alkyl;

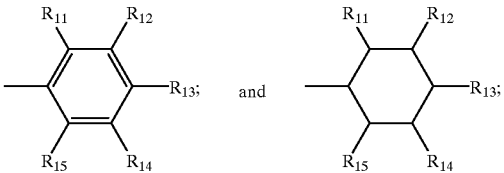

wherein each of R$_{11}$, R$_{12}$, R$_{13}$, R$_{14}$, and R$_{15}$ is independently CH$_3$, hydrogen, halogen, OH, SH, NH$_2$, or NO$_2$.

12. An analgesic compound according to anyone of claims 1 to 5 wherein;
R$_4$ is selected from the group consisting of: —CH$_3$; —C(CH$_3$)$_3$; —CH(CH$_3$)$_2$;

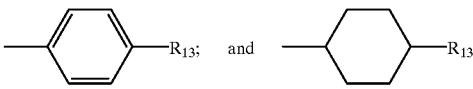

wherein R$_{13}$ is as defined in claim 11.

13. An analgesic compound according to anyone of claims 1 to 5 wherein;
R$_4$ is selected from the group consisting of:

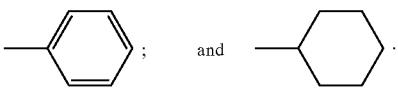

14. An analgesic compound selected from the group consisting of:
2-R-(2-Amino-3-(4-Hydroxy-2,6-dimethyl-phenyl)-propionyl)-1,2,3,4-tetrahydro-isoquinoline-3-S-carboxylic acid (2-hydroxy-3-phenyl-propyl)amide trifluoroacetic salt (racemic mixture) compound #1;
2-R-(2-Amino-3-(4-Hydroxy-2,6-dimethyl-phenyl)-propionyl)-1,2,3,4-tetrahydro-isoquinoline-3-S-carboxylic acid (2-hydroxy-3-phenyl-propyl)amide trifluoroacetic salt (fast isomer) compound #1A;
2-R-(2-Amino-3-(4-hydroxy-2,6-dimethyl-phenyl)-propionyl)-1,2,3,4-tetrahydro-isoquinoline-3-S-carboxylic acid (2-hydroxy-3-phenyl-propyl)amide trifluoroacetic salt (slow isomer) Compound 1B;
2-S-(2-Amino-3-(4-hydroxy-2,6-dimethyl-phenyl)-propionyl)-7-hydroxy1,2,3,4-tetrahydro-isoquinoline-3-S-carboxylic acid (2-hydroxy-3-phenyl-propyl)amide trifluoroacetic salt (racemic mixture) compound #2;
2-(2-Guanidino-3-(4-hydroxy-2,6-dimethyl-phenyl)-propionyl)-1,2,3,4-tetrahydro-isoquinoline-3-S-carboxylic acid (2-R-hydroxy-3-phenyl-propyl)-amide ditrifloroacetic salt (racemic mixture) compound #3;
2-(2-Guanidino-3-(4-hydroxy-2,6-dimethyl-phenyl)-propionyl)-1,2,3,4-tetrahydro-isoquinoline-3-S-carboxylic acid (2-R-hydroxy-3-phenyl-propyl)-amide ditrifloroacetic salt (fast isomer) compound #3A;
2-(2-Guanidino-3-(4-hydroxy-2,6-dimethyl-phenyl)-propionyl)-1,2,3,4-tetrahydro-isoquinoline-3-S-carboxylic acid (2-R-hydroxy-3-phenyl-propyl)-amide ditrifloroacetic salt (slow isomer) compound #3B;

2-S-(2-Amino-3-(4-hydroxy-2,6-dimethyl-phenyl)-propionyl)-1,2,3,4-tetrahydro-isoquinoline-3-S-carboxylic acid (2-hydroxy-3-phenyl-propyl)amide trifluoroacetic salt (racemic mixture) of compound #4;

2-S-(2-Amino-3-(4-hydroxy-2,6-dimethyl-phenyl)-propionyl)-1,2,3,4-tetrahydro-isoquinoline-3-S-carboxylic acid (2-hydroxy-3-phenyl-propyl)amide trifluoroacetic salt (fast isomer) of compound # 4A;

2-S-(2-Amino-3-(4-hydroxy-2,6-dimethyl-phenyl)-propionyl)-1,2,3,4-tetrahydro-isoquinoline-3-S-carboxylic acid (2-hydroxy-3-phenyl-propyl)amide trifluoroacetic salt (slow isomer) Compound #4B;

S-2-(2-Amino-3-(hydroxy-phenyl)-S-1,2,3,4-tetrahydroisoquinoline-carboxylic acid (R-2-hydroxy-3-phenyl-propyl)-amide hydrochloride acid (racemic mixture) compound #8;

S-2-(2-Amino-3-(hydroxy-phenyl)-S-1,2,3,4-tetrahydroisoquinoline-carboxylic acid (R-2-hydroxy-3-phenyl-propyl)-amide hydrochloride acid (slow isomer) compound #8a;

2-S-Amino-3-(4-hydroxy-phenyl)-1-{3-(R-2-hydroxy-3-phenyl-propylamino)-methyl)-S-3,4-dihydro-1H-isoquinolin-2-yl}propan-1-one ditrifluoroacetic salt (fast isomer) compound #9A ;

2-(tyrosyl)-3S-(D-phenylalanamido methyl)-1,2,3,4-tetrahydro isoquinoline hydro chloride salt compound #10A;

2-(tyrosyl)-3S-phenylalanamido methyl)-1,2,3,4-tetrahydro isoquinoline hydro chloride salt compound #11A; 2-Tyrosyl-3S-tyrosamidomethyl-1,2,3,4-tetrahydroisoquinoline hydrochloride salt compound #12A;

2-Tyrosyl-3-benzoxycarboxamidomethyl-1,2,3,4-tetrahydroisoquinoline hydrochloride salt compound #13A;

trans-2-(3-(4-hydroxy-phenyl)-pyrrolidine-2-carbonyl-S-1,2,3,4-tetrahydroquinoline-3-carboxylic acid (R-2-hydroxy-3-phenyl-propyl)amide trifluoroacetic salt compound #14;

trans-2-(3-(4-hydroxy-phenyl)-pyrrolidine-2-carbonyl-S-1,2,3,4-tetrahydroquinoline-3-carboxylic acid (R-2-hydroxy-3-phenyl-propyl)amide trifluoroacetic salt (fast isomer) compound #14A;

trans-2-(3-(4-hydroxy-phenyl)-pyrrolidine-2-carbonyl-S-1,2,3,4-tetrahydroquinoline-3-carboxylic acid (R-2-hydroxy-3-phenyl-propyl)amide trifluoroacetic salt (slow isomer) compound #14B;

and pharmaceutically acceptable salts thereof.

15. An analgesic compound selected from the group consisting of:

2-R-(2-Amino-3-(4-hydroxy-2,6-dimethyl-phenyl)-propionyl)-1,2,3,4-tetrahydro-isoquinoline-3-S-carboxylic acid (2-hydroxy-3-phenyl-propyl)amide trifluoroacetic salt (slow isomer)

Compound 1B; 2-S-(2-Amino-3-(4-hydroxy-2,6-dimethyl-phenyl)-propionyl)-7-hydroxy1,2,3,4-tetrahydro-isoquinoline-3-S-carboxylic acid (2-hydroxy-3-phenyl-propyl)amide trifluoroacetic salt (racemic mixture) compound #2;

2-(2-Guanidino-3-(4-hydroxy-2,6-dimethyl-phenyl)-propionyl)-1,2,3,4-tetrahydro-isoquinoline-3-S-carboxylic acid (2-R-hydroxy-3-phenyl-propyl)-amide ditrifloroacetic salt (fast isomer) compound #3A;

2-(2-Guanidino-3-(4-hydroxy-2,6-dimethyl-phenyl)-propionyl)-1,2,3,4-tetrahydro-isoquinoline-3-S-carboxylic acid (2-R-hydroxy-3-phenyl-propyl)-amide ditrifloroacetic salt (slow isomer) compound #3B;

2-S-(2-Amino-3-(4-hydroxy-2,6-dimethyl-phenyl)-propionyl)-1,2,3,4-tetrahydro-isoquinoline-3-S-carboxylic acid (2-hydroxy-3-phenyl-propyl)amide trifluoroacetic salt (fast isomer) of compound #4A;

2-S-(2-Amino-3-(4-hydroxy-2,6-dimethyl-phenyl)-propionyl)-1,2,3,4-tetrahydro-isoquinoline-3-S-carboxylic acid (2-hydroxy-3-phenyl-propyl)amide trifluoroacetic salt (slow isomer) Compound #4B;

and pharmaceutically acceptable derivatives thereof.

16. An analgesic compound:

2-(2-Guanidino-3-(4-hydroxy-2,6-dimethyl-phenyl)-propionyl)-1,2,3,4-tetrahydro-isoquinoline-3-S-carboxylic acid (2-R-hydroxy-3-phenyl-propyl)-amide ditrifloroacetic salt (fast isomer) compound #3a; and pharmaceutically acceptable salts thereof.

17. A pharmaceutically acceptable composition comprising an analgesic compound according to anyone of claims 1 to 5 or 14 to 16.

18. A method of providing analgesia to a patient, comprising administering an effective amount of a compound as described in claim 1 wherein;

L is a $C_{1-12}$ alkyl chain which can be substituted with at least one substituent selected from the group consisting of a $C_3$–$C_{12}$ heterocycle containing at least one heteroatom selected from the group consisting of O, N, and S;; $C_{1-6}$ alkyl; $OR_{31}$ wherein, $R_{31}$ is hydrogen or $C_{1-6}$ alkyl; $SR_{32}$ wherein, $R_{32}$ is hydrogen or $C_{1-6}$ alkyl; —NHC(O)$R_{33}$ wherein, $R_{33}$ is $C_{6-12}$ aryl, $C_{7-18}$ aralkyl or $C_{1-6}$ alkyl; —OC(O)$R_{34}$ wherein, $R_{34}$ is hydrogen, $C_{6-12}$ aryl, $C_{7-18}$ aralkyl, $C_{1-6}$ alkyl, —NHR$_{35}$ wherein, $R_{35}$ is hydrogen, $C_{6-12}$ aryl or $C_{1-6}$ alkyl; and NR$_6$R$_7$, wherein each of $R_6$ and $R_7$ is independently hydrogen or $C_{1-6}$ alkyl.

19. A method of providing analgesia to a patient, comprising administering an effective amount of a compound selected from the group consisting of:

2-(2-Amino-3-(4-Hydroxy-2,6-dimethyl-phenyl)-propionyl)-1,2,3,4-tetrahydroisoquinoline-3-S-carboxylic acid (3-phenyl-propyl) amide trifluoroacetic salt (racemic mixture) compound #5;

2-(2-Amino-3-(4-Hydroxy-2,6-dimethyl-phenyl)-propionyl)-1,2,3,4-tetrahydroisoquinoline-3-S-carboxylic acid (3-phenyl-propyl) amide trifluoroacetic salt (fast isomer) compound #5a;

2-(2-Amino-3-(4-Hydroxy-2,6-dimethyl-phenyl)-propionyl)-1,2,3,4-tetrahydroisoquinoline-3-carboxylic acid (3-phenyl-propyl) amide trifluoroacetic salt compound #5b;

2-(2-Amino-3-(4-Hydroxy-2,6-dimethyl-phenyl)-propionyl)-1,2,3,4tetrahydroisoquinoline-3-S-carboxylic acid (3-phenyl-propyl) amide trifluoroacetic salt (racemic mixture) compound #6;

2-(2-Amino-3-(4-Hydroxy-2,6-dimethyl-phenyl)-propionyl)-1,2,3,4-tetrahydroisoquinoline-3-S-carboxylic acid (3-phenyl-propyl) amide trifluoroacetic salt (fast isomer) compound #6A;

2-(2-Amino-3-(4-Hydroxy-2,6-dimethyl-phenyl)-propionyl)-1,2,3,4-tetrahydroisoquinoline-3-S-carboxylic acid (3-phenyl-propyl) amide trifluoroacetic salt (slow isomer) compound #6B;

2-(2-Amino-3-(4-hydroxy-2,6-dimethyl-phenyl)-propionyl)-1,2,3,4-tetrahydroisoquinoline-3-S-carboxylic acid (2-fluoro-(4-phenyl-ethyl) amide trifluoroacetic salt (racemic mixture) compound #7

2-(2-Amino-3-(4hydroxy-2,6-dimethyl-phenyl)-propionyl)-1,2,3,4-tetrahydroisoquinoline-3-S-carboxylic acid (2-fluoro-(4-phenyl-ethyl) amide trifluoroacetic salt (fast isomer) compound #7A;

2-(2-Amino-3-(4hydroxy-2,6-dimethyl-phenyl)-propionyl)-1,2,3,4-tetrahydroisoquinoline-3-S-carboxylic acid (2-fluoro-(4-phenyl-ethyl) amide trifluoroacetic salt (slow isomer) compound #7B;

and pharmaceutically acceptable salts thereof.

20. The method according to claim 18 wherein said compound is selected from the group consisting of:

2-(2-Amino-3-(4-Hydroxy-2,6-dimethyl-phenyl)-propionyl)-1,2,3,4-tetrahydro-isoquinoline-3-S-carboxylic acid (3-phenyl-propyl)amide trifluoroacetic salt (fast isomer) compound #5A; and 2-(2-Amino-3-(4-Hydroxy-2,6-dimethyl-phenyl)-propionyl)-1,2,3,4-tetrahydro-isoquinoline-3-carboxylic acid (3-phenyl-propyl)amide trifluoroacetic salt compound #5B;

2-(2-Amino-3-(4-hydroxy-2,6-dimethyl-phenyl)-propionyl)-1,2,3,4-tetrahydro-isoquinoline-3-S-carboxylic acid (2-fluoro-(4-phenyl-ethyl)amide trifluoroacetic salt (fast isomer) compound #7A;

and pharmaceutically acceptable salts thereof.

* * * * *